United States Patent [19]

Franco et al.

[11] Patent Number: 6,140,485

[45] Date of Patent: Oct. 31, 2000

[54] NUCLEIC ACID ENCODING HUMAN NEURONAL CALCIUM CHANNEL SUBUNITS

[75] Inventors: Rodrigo Franco, Basking Ridge; Ai Ru Sun Chen, Piscataway; David John Shuey, Plainsboro, all of N.J.

[73] Assignee: American Home Products Corp., Wayne, N.J.

[21] Appl. No.: 09/452,007

[22] Filed: Nov. 30, 1999

Related U.S. Application Data

[62] Division of application No. 08/713,118, Sep. 16, 1996, Pat. No. 6,040,436.

[51] Int. Cl.$^7$ .................................................. C07H 21/02
[52] U.S. Cl. ..................... 536/23.1; 536/22.1; 536/24.1; 536/24.3; 536/24.33; 435/6; 435/69.1; 435/240.2; 435/810; 935/77; 935/78
[58] Field of Search ................................. 536/23.1, 22.1, 536/24.1, 24.3, 24.33; 435/6, 69.1, 240.2, 810; 935/77, 78

[56] References Cited

U.S. PATENT DOCUMENTS 5,792,846  8/1998  Harpold et al. ........................ 536/23.1

FOREIGN PATENT DOCUMENTS

| 0 507 170 A2 | 3/1992 | European Pat. Off. . |
| WO 93/04083 | 3/1993 | WIPO . |
| WO 95/04822 | 2/1995 | WIPO . |

OTHER PUBLICATIONS

Collin, T. et al., "Cloning, Chromosomal Location and Functional Expression of the Human Voltage–Dependent Calcium–Channel β3 Subunit," *Eur. J. Biochem.* 220: 257–262 (1994).

Williams, M. E. et al., "Structure and Functional Expression of $\alpha_1$, $\alpha_2$, and β Subunits of a Novel Human Neuronal Calcium Channel Subtype," *Neuron.* 8: 71–84 (1992).

Williams, M. D. et al., "Structural and Functional Expression of an ω–Conotoxin–Sensitive Human N–Type Calcium Channel," *Science* 257: 389–395 (1992).

Abstract: Society for Neuroscience, Meeting, Nov. 1994, Miami, FL; *Soc. For Neuroscience Abstracts* 20: 34.10 (1994).

GenBank Assession #M94172.

GenBank Assession #L27594.

GenBank Assession #M76559.

*Primary Examiner*—W. Gary Jones
*Assistant Examiner*—Janell E. Taylor
*Attorney, Agent, or Firm*—Hamilton, Brook, Smith & Brook, Reynolds, P.C.

[57] ABSTRACT

Nucleic acids encoding each of three subunits, α1B, α2δ, and β3, of a calcium channel, are disclosed. Also disclosed are vectors containing the nucleic acids encoding the subunits; host cells containing the nucleic acids encoding the subunits; methods of isolating nucleic acids encoding related calcium channel subunits; the subunit proteins; fusion proteins comprising the subunit proteins; antibodies to the subunit proteins; assays to identify agents that modulate calcium channel activity, and agents identified thereby; methods of treating certain central nervous system disorders by altering calcium channel activity; and methods of diagnosing diseases associated with particular calcium channels, such as Lambert-Eaton syndrome.

14 Claims, 1 Drawing Sheet

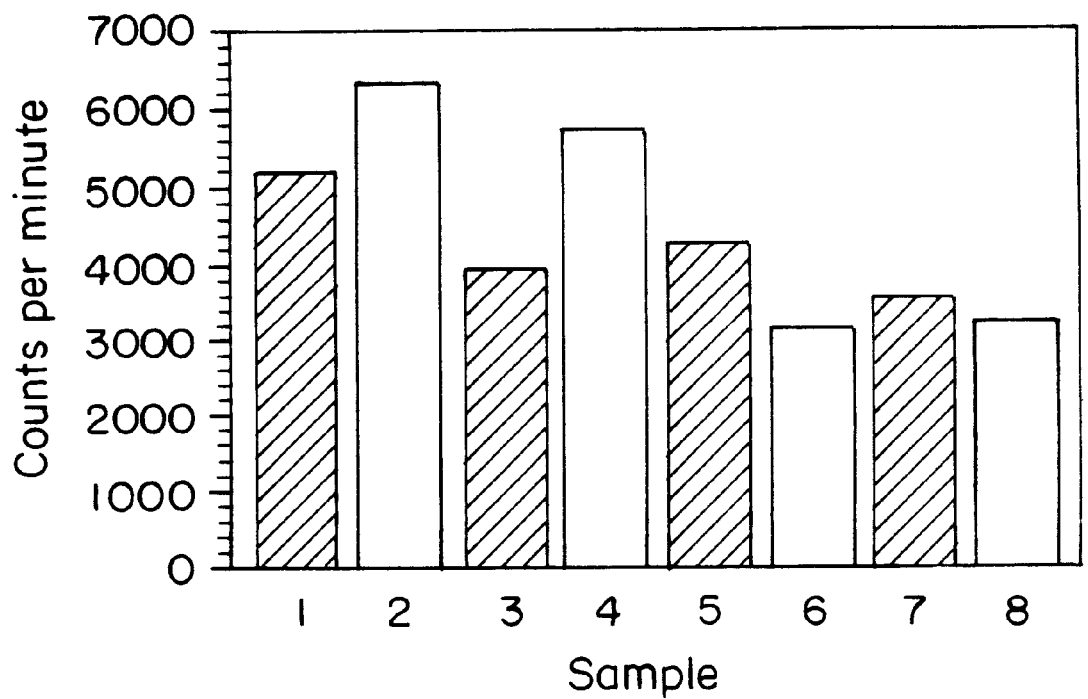

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 7266 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 92..7102

(xi) SEQUENCE DESCRIPTION: SEQ ID NO:1:

```
TCCGTGGCTG CTCCGCTCTG AGCGCCTGGC GCGCCCCGCG CCCTCCCTGC CGGGGCCGCT        60

GGGCCGGGGA TGCACGCGGG GCCCGGGAGC C ATG GTC CGC TTC GGG GAC GAG         112
                                 Met Val Arg Phe Gly Asp Glu
                                  1               5

CTG GGC GGC CGC TAT GGA GGC CCC GGC AGC GGA GAG CGG GCC CGG GGC        160
Leu Gly Gly Arg Tyr Gly Gly Pro Gly Ser Gly Glu Arg Ala Arg Gly
        10                  15                  20

GGC GGG GCC GGC GGG GCG GGG GGC CCG GGT CCC GGG GGG CTG CAG CCC        208
Gly Gly Ala Gly Gly Ala Gly Gly Pro Gly Pro Gly Gly Leu Gln Pro
    25                  30                  35
```

-continued

```
GGC CAG CGG GTC CTC TAC AAG CAA TCG ATC GCG CAG CGC GCG CGG ACC         256
Gly Gln Arg Val Leu Tyr Lys Gln Ser Ile Ala Gln Arg Ala Arg Thr
 40              45                  50                  55

ATG GCG CTG TAC AAC CCC ATC CCG GTC AAG CAG AAC TGC TTC ACC GTC         304
Met Ala Leu Tyr Asn Pro Ile Pro Val Lys Gln Asn Cys Phe Thr Val
                 60                  65                  70

AAC CGC TCG CTC TTC GTC TTC AGC GAG GAC AAC GTC GTC CGC AAA TAC         352
Asn Arg Ser Leu Phe Val Phe Ser Glu Asp Asn Val Val Arg Lys Tyr
             75                  80                  85

GCG AAG CGC ATC ACC GAG TGG CCT CCA TTC GAG TAT ATG ATC CTG GCC         400
Ala Lys Arg Ile Thr Glu Trp Pro Pro Phe Glu Tyr Met Ile Leu Ala
         90                  95                 100

ACC ATC ATC GCC AAC TGC ATC GTG CTG GCC CTG GAG CAG CAC CTC CCT         448
Thr Ile Ile Ala Asn Cys Ile Val Leu Ala Leu Glu Gln His Leu Pro
     105                 110                 115

GAT GGG GAC AAA ACG CCC ATG TCC GAG CGG CTG GAC GAC ACG GAG CCC         496
Asp Gly Asp Lys Thr Pro Met Ser Glu Arg Leu Asp Asp Thr Glu Pro
120                 125                 130                 135

TAT TTC ATC GGG ATC TTT TGC TTC GAG GCA GGG ATC AAA ATC ATC GCT         544
Tyr Phe Ile Gly Ile Phe Cys Phe Glu Ala Gly Ile Lys Ile Ile Ala
                140                 145                 150

CTG GGC TTT GTC TTC CAC AAG GGC TCT TAC CTG CGG AAC GGC TGG AAC         592
Leu Gly Phe Val Phe His Lys Gly Ser Tyr Leu Arg Asn Gly Trp Asn
            155                 160                 165

GTC ATG GAC TTC GTG GTC GTC CTC ACA GGG ATC CTT GCC ACG GCT GGA         640
Val Met Asp Phe Val Val Val Leu Thr Gly Ile Leu Ala Thr Ala Gly
        170                 175                 180

ACT GAC TTC GAC CTG CGA ACA CTG AGG GCT GTG CGT GTG CTG AGG CCC         688
Thr Asp Phe Asp Leu Arg Thr Leu Arg Ala Val Arg Val Leu Arg Pro
185                 190                 195

CTG AAG CTG GTG TCT GGG ATT CCA AGT TTG CAG GTG GTG CTC AAG TCC         736
Leu Lys Leu Val Ser Gly Ile Pro Ser Leu Gln Val Val Leu Lys Ser
200                 205                 210                 215

ATC ATG AAG GCC ATG GTT CCA CTC CTG CAG ATT GGG CTG CTT CTC TTC         784
Ile Met Lys Ala Met Val Pro Leu Leu Gln Ile Gly Leu Leu Leu Phe
                220                 225                 230

TTT GCC ATC CTC ATG TTT GCC ATC ATT GGC CTG GAG TTC TAC ATG GGC         832
Phe Ala Ile Leu Met Phe Ala Ile Ile Gly Leu Glu Phe Tyr Met Gly
            235                 240                 245

AAG TTC CAC AAG GCC TGT TTC CCC AAC AGC ACA GAT GCG GAG CCC GTG         880
Lys Phe His Lys Ala Cys Phe Pro Asn Ser Thr Asp Ala Glu Pro Val
        250                 255                 260

GGT GAC TTC CCC TGT GGC AAG GAG GCC CCA GCC CGG CTG TGC GAG GGC         928
Gly Asp Phe Pro Cys Gly Lys Glu Ala Pro Ala Arg Leu Cys Glu Gly
265                 270                 275

GAC ACT GAG TGC CGG GAG TAC TGG CCA GGA CCC AAC TTT GGC ATC ACC         976
Asp Thr Glu Cys Arg Glu Tyr Trp Pro Gly Pro Asn Phe Gly Ile Thr
280                 285                 290                 295

AAC TTT GAC AAT ATC CTG TTT GCC ATC TTG ACG GTG TTC CAG TGC ATC        1024
Asn Phe Asp Asn Ile Leu Phe Ala Ile Leu Thr Val Phe Gln Cys Ile
                300                 305                 310

ACC ATG GAG GGC TGG ACT GAC ATC CTC TAT AAT ACA AAC GAT GCG GCC        1072
Thr Met Glu Gly Trp Thr Asp Ile Leu Tyr Asn Thr Asn Asp Ala Ala
            315                 320                 325

GGC AAC ACC TGG AAC TGG CTC TAC TTC ATC CCT CTC ATC ATC ATC GGC        1120
Gly Asn Thr Trp Asn Trp Leu Tyr Phe Ile Pro Leu Ile Ile Ile Gly
        330                 335                 340

TCC TTC TTC ATG CTC AAC CTG GTG CTG GGC GTG CTC TCG GGG GAG TTT        1168
Ser Phe Phe Met Leu Asn Leu Val Leu Gly Val Leu Ser Gly Glu Phe
345                 350                 355
```

```
GCC AAG GAG CGA GAG AGG GTG GAG AAC CGC CGC GCC TTC CTG AAG CTG    1216
Ala Lys Glu Arg Glu Arg Val Glu Asn Arg Arg Ala Phe Leu Lys Leu
360                 365                 370                 375

CGC CGG CAG CAG CAG ATC GAG CGA GAG CTC AAC GGG TAC CTG GAG TGG    1264
Arg Arg Gln Gln Gln Ile Glu Arg Glu Leu Asn Gly Tyr Leu Glu Trp
                380                 385                 390

ATC TTC AAG GCG GAG GAA GTC ATG CTG GCC GAG GAG GAC AGG AAT GCA    1312
Ile Phe Lys Ala Glu Glu Val Met Leu Ala Glu Glu Asp Arg Asn Ala
            395                 400                 405

GAG GAG AAG TCC CCT TTG GAC GTG CTG AAG AGA GCG GCC ACC AAG AAG    1360
Glu Glu Lys Ser Pro Leu Asp Val Leu Lys Arg Ala Ala Thr Lys Lys
        410                 415                 420

AGC AGA AAT GAC CTG ATC CAC GCA GAG GAG GGA GAG GAC CGG TTT GCA    1408
Ser Arg Asn Asp Leu Ile His Ala Glu Glu Gly Glu Asp Arg Phe Ala
    425                 430                 435

GAT CTC TGT GCT GTT GGA TCC CCC TTC GCC CGC GCC AGC CTC AAG AGC    1456
Asp Leu Cys Ala Val Gly Ser Pro Phe Ala Arg Ala Ser Leu Lys Ser
440                 445                 450                 455

GGG AAG ACA GAG AGC TCG TCA TAC TTC CGG AGG AAG GAG AAG ATG TTC    1504
Gly Lys Thr Glu Ser Ser Ser Tyr Phe Arg Arg Lys Glu Lys Met Phe
                460                 465                 470

CGG TTT TTT ATC CGG CGC ATG GTG AAG GCT CAG AGC TTC TAC TGG GTG    1552
Arg Phe Phe Ile Arg Arg Met Val Lys Ala Gln Ser Phe Tyr Trp Val
            475                 480                 485

GTG CTG TGC GTG GTG GCC CTG AAC ACA CTG TGT GTG GCC ATG GTG CAT    1600
Val Leu Cys Val Val Ala Leu Asn Thr Leu Cys Val Ala Met Val His
        490                 495                 500

TAC AAC CAG CCG CGG CGG CTT ACC ACG ACC CTG TAT TTT GCA GAG TTT    1648
Tyr Asn Gln Pro Arg Arg Leu Thr Thr Thr Leu Tyr Phe Ala Glu Phe
    505                 510                 515

GTT TTC CTG GGT CTC TTC CTC ACA GAG ATG TCC CTG AAG ATG TAT GGC    1696
Val Phe Leu Gly Leu Phe Leu Thr Glu Met Ser Leu Lys Met Tyr Gly
520                 525                 530                 535

CTG GGG CCC AGA AGC TAC TTC CGG TCC TCC TTC AAC TGC TTC GAC TTT    1744
Leu Gly Pro Arg Ser Tyr Phe Arg Ser Ser Phe Asn Cys Phe Asp Phe
                540                 545                 550

GGG GTC ATC GTG GGG AGC GTC TTT GAA GTG GTC TGG GCG GCC ATC AAG    1792
Gly Val Ile Val Gly Ser Val Phe Glu Val Val Trp Ala Ala Ile Lys
            555                 560                 565

CCG GGA AGC TCC TTT GGG ATC AGT GTG CTG CGG GCC CTC CGC CTG CTG    1840
Pro Gly Ser Ser Phe Gly Ile Ser Val Leu Arg Ala Leu Arg Leu Leu
        570                 575                 580

AGG ATC TTC AAA GTC ACG AAG TAC TGG AGC TCC CTG CGG AAC CTG GTG    1888
Arg Ile Phe Lys Val Thr Lys Tyr Trp Ser Ser Leu Arg Asn Leu Val
    585                 590                 595

GTG TCC CTG CTG AAC TCC ATG AAG TCC ATC ATC AGC CTG CTC TTC TTG    1936
Val Ser Leu Leu Asn Ser Met Lys Ser Ile Ile Ser Leu Leu Phe Leu
600                 605                 610                 615

CTC TTC CTG TTC ATT GTG GTC TTC GCC CTG CTG GGG ATG CAG CTG TTT    1984
Leu Phe Leu Phe Ile Val Val Phe Ala Leu Leu Gly Met Gln Leu Phe
                620                 625                 630

GGG GGA CAG TTC AAC TTC CAG GAT GAG ACT CCC ACA ACC AAC TTC GAC    2032
Gly Gly Gln Phe Asn Phe Gln Asp Glu Thr Pro Thr Thr Asn Phe Asp
            635                 640                 645

ACC TTC CCT GCC GCC ATC CTC ACT GTC TTC CAG ATC CTG ACG GGA GAG    2080
Thr Phe Pro Ala Ala Ile Leu Thr Val Phe Gln Ile Leu Thr Gly Glu
        650                 655                 660
```

```
GAC TGG AAT GCA GTG ATG TAT CAC GGG ATC GAA TCG CAA GGC GGC GTC        2128
Asp Trp Asn Ala Val Met Tyr His Gly Ile Glu Ser Gln Gly Gly Val
            665                 670                 675

AGC AAA GGC ATG TTC TCG TCC TTT TAC TTC ATT GTC CTG ACA CTG TTC        2176
Ser Lys Gly Met Phe Ser Ser Phe Tyr Phe Ile Val Leu Thr Leu Phe
680                 685                 690                 695

GGA AAC TAC ACT CTG CTG AAT GTC TTT CTG GCC ATC GCT GTG GAC AAC        2224
Gly Asn Tyr Thr Leu Leu Asn Val Phe Leu Ala Ile Ala Val Asp Asn
                    700                 705                 710

CTG GCC AAC GCC CAA GAG CTG ACC AAG GAT GAA GAG GAG ATG GAA GAA        2272
Leu Ala Asn Ala Gln Glu Leu Thr Lys Asp Glu Glu Glu Met Glu Glu
                715                 720                 725

GCA GCC AAT CAG AAG CTT GCT CTG CAA AAG GCC AAA GAA GTG GCT GAA        2320
Ala Ala Asn Gln Lys Leu Ala Leu Gln Lys Ala Lys Glu Val Ala Glu
            730                 735                 740

GTC AGC CCC ATG TCT GCC GCG AAC ATC TCC ATC GCC GCC AGG CAG CAG        2368
Val Ser Pro Met Ser Ala Ala Asn Ile Ser Ile Ala Ala Arg Gln Gln
745                 750                 755

AAC TCG GCC AAG GCG CGC TCG GTG TGG GAG CAG CGG GCC AGC CAG CTA        2416
Asn Ser Ala Lys Ala Arg Ser Val Trp Glu Gln Arg Ala Ser Gln Leu
760                 765                 770                 775

CGG CTG CAG AAC CTG CGG GCC AGC TGC GAG GCG CTG TAC AGC GAG ATG        2464
Arg Leu Gln Asn Leu Arg Ala Ser Cys Glu Ala Leu Tyr Ser Glu Met
                    780                 785                 790

GAC CCC GAG GAG CGG CTG CGC TTC GCC ACT ACG CGC CAC CGG CGG CCC        2512
Asp Pro Glu Glu Arg Leu Arg Phe Ala Thr Thr Arg His Arg Arg Pro
                795                 800                 805

GAC ATG AAG ACG CAC CTG GAC CGG CCG CTG GTG GTG GAG CTG GGC CGC        2560
Asp Met Lys Thr His Leu Asp Arg Pro Leu Val Val Glu Leu Gly Arg
            810                 815                 820

GAC GGC GCG CGG GGG CCC GTG GGA GGC AAA GCC CGA CCT GAG GCT GCG        2608
Asp Gly Ala Arg Gly Pro Val Gly Gly Lys Ala Arg Pro Glu Ala Ala
825                 830                 835

GAG GCC CCC GAG GGC GTC GAC CCT CCG CGC AGG CAC CAC CGG CAC CGC        2656
Glu Ala Pro Glu Gly Val Asp Pro Pro Arg Arg His His Arg His Arg
840                 845                 850                 855

GAC AAG GAC AAG ACC CCC GCG GCG GGG GAC CAG GAC CGA GCA GAG GCC        2704
Asp Lys Asp Lys Thr Pro Ala Ala Gly Asp Gln Asp Arg Ala Glu Ala
                    860                 865                 870

CCG AAG GCG GAG AGC GGG GAG CCC GGT GCC CGG GAG GAG CGG CCG CGG        2752
Pro Lys Ala Glu Ser Gly Glu Pro Gly Ala Arg Glu Glu Arg Pro Arg
                875                 880                 885

CCG CAC CGC AGC CAC AGC AAG GAG GCC GCG GGG CCC CCG GAG GCG CGG        2800
Pro His Arg Ser His Ser Lys Glu Ala Ala Gly Pro Pro Glu Ala Arg
            890                 895                 900

AGC GAG CGC GGC CGA GGC CCA GGC CCC GAG GGC GGC CGG CGG CAC CAC        2848
Ser Glu Arg Gly Arg Gly Pro Gly Pro Glu Gly Gly Arg Arg His His
905                 910                 915

CGG CGC GGC TCC CCG GAG GAG GCG GCC GAG CGG GAG CCC GA CGC CAC         2896
Arg Arg Gly Ser Pro Glu Glu Ala Ala Glu Arg Glu Pro Arg Arg His
920                 925                 930                 935

CGC GCG CAC CGG CAC CAG GAT CCG AGC AAG GAG TGC GCC GGC GCC AAG        2944
Arg Ala His Arg His Gln Asp Pro Ser Lys Glu Cys Ala Gly Ala Lys
                    940                 945                 950

GGC GAG CGG CGC GCG CGG CAC CGC GGC GGC CCC CGA GCG GGG CCC CGG        2992
Gly Glu Arg Arg Ala Arg His Arg Gly Gly Pro Arg Ala Gly Pro Arg
                955                 960                 965

GAG GCG GAG AGC GGG GAG GAG CCG GCG CGG CGG CAC CGG GCC CGG CAC        3040
Glu Ala Glu Ser Gly Glu Glu Pro Ala Arg Arg His Arg Ala Arg His
                970                 975                 980
```

-continued

```
AAG GCG CAG CCT GCT CAC GAG GCT GTG GAG AAG GAG ACC ACG GAG AAG    3088
Lys Ala Gln Pro Ala His Glu Ala Val Glu Lys Glu Thr Thr Glu Lys
    985                 990                 995

GAG GCC ACG GAG AAG GAG GCT GAG ATA GTG GAA GCC GAC AAG GAA AAG    3136
Glu Ala Thr Glu Lys Glu Ala Glu Ile Val Glu Ala Asp Lys Glu Lys
1000                1005                1010                1015

GAG CTC CGG AAC CAC CAG CCC CGG GAG CCA CAC TGT GAC CTG GAG ACC    3184
Glu Leu Arg Asn His Gln Pro Arg Glu Pro His Cys Asp Leu Glu Thr
                1020                1025                1030

AGT GGG ACT GTG ACT GTG GGT CCC ATG CAC ACA CTG CCC AGC ACC TGT    3232
Ser Gly Thr Val Thr Val Gly Pro Met His Thr Leu Pro Ser Thr Cys
            1035                1040                1045

CTC CAG AAG GTG GAG GAA CAG CCA GAG GAT GCA GAC AAT CAG CGG AAC    3280
Leu Gln Lys Val Glu Glu Gln Pro Glu Asp Ala Asp Asn Gln Arg Asn
        1050                1055                1060

GTC ACT CGC ATG GGC AGT CAG CCC CCA GAC CCG AAC ACT ATT GTA CAT    3328
Val Thr Arg Met Gly Ser Gln Pro Pro Asp Pro Asn Thr Ile Val His
    1065                1070                1075

ATC CCA GTG ATG CTG ACG GGC CCT CTT GGG GAA GCC ACG GTC GTT CCC    3376
Ile Pro Val Met Leu Thr Gly Pro Leu Gly Glu Ala Thr Val Val Pro
1080                1085                1090                1095

AGT GGT AAC GTG GAC CTG GAA AGC CAA GCA GAG GGG AAG AAG GAG GTG    3424
Ser Gly Asn Val Asp Leu Glu Ser Gln Ala Glu Gly Lys Lys Glu Val
                1100                1105                1110

GAA GCG GAT GAC GTG ATG AGG AGC GGC CCC CGG CCT ATC GTC CCA TAC    3472
Glu Ala Asp Asp Val Met Arg Ser Gly Pro Arg Pro Ile Val Pro Tyr
            1115                1120                1125

AGC TCC ATG TTC TGT TTA AGC CCC ACC AAC CTG CTC CGC CGC TTC TGC    3520
Ser Ser Met Phe Cys Leu Ser Pro Thr Asn Leu Leu Arg Arg Phe Cys
        1130                1135                1140

CAC TAC ATC GTG ACC ATG AGG TAC TTC GAG GTG GTC ATT CTC GTG GTC    3568
His Tyr Ile Val Thr Met Arg Tyr Phe Glu Val Val Ile Leu Val Val
    1145                1150                1155

ATC GCC TTG AGC AGC ATC GCC CTG GCT GCT GAG GAC CCA GTG CGC ACA    3616
Ile Ala Leu Ser Ser Ile Ala Leu Ala Ala Glu Asp Pro Val Arg Thr
1160                1165                1170                1175

GAC TCG CCC AGG AAC AAC GCT CTG AAA TAC CTG GAT TAC ATT TTC ACT    3664
Asp Ser Pro Arg Asn Asn Ala Leu Lys Tyr Leu Asp Tyr Ile Phe Thr
                1180                1185                1190

GGT GTC TTT ACC TTT GAG ATG GTG ATA AAG ATG ATC GAC TTG GGA CTG    3712
Gly Val Phe Thr Phe Glu Met Val Ile Lys Met Ile Asp Leu Gly Leu
            1195                1200                1205

CTG CTT CAC CCT GGA GCC TAT TTC CGG GAC TTG TGG AAC ATT CTG GAC    3760
Leu Leu His Pro Gly Ala Tyr Phe Arg Asp Leu Trp Asn Ile Leu Asp
        1210                1215                1220

TTC ATT GTG GTC AGT GGC GCC CTG GTG GCG TTT GCT TTC TCA GGA TCC    3808
Phe Ile Val Val Ser Gly Ala Leu Val Ala Phe Ala Phe Ser Gly Ser
    1225                1230                1235

AAA GGG AAA GAC ATC AAT ACC ATC AAG TCT CTG AGA GTC CTT CGT GTC    3856
Lys Gly Lys Asp Ile Asn Thr Ile Lys Ser Leu Arg Val Leu Arg Val
1240                1245                1250                1255

CTG CGG CCC CTC AAG ACC ATC AAA CGG CTG CCC AAG CTC AAG GCT GTG    3904
Leu Arg Pro Leu Lys Thr Ile Lys Arg Leu Pro Lys Leu Lys Ala Val
                1260                1265                1270

TTT GAC TGT GTG GTG AAC TCC CTG AAG AAT GTC CTC AAC ATC TTG ATT    3952
Phe Asp Cys Val Val Asn Ser Leu Lys Asn Val Leu Asn Ile Leu Ile
            1275                1280                1285
```

-continued

| | |
|---|---|
| GTC TAC ATG CTC TTC ATG TTC ATA TTT GCC GTC ATT GCG GTG CAG CTC<br>Val Tyr Met Leu Phe Met Phe Ile Phe Ala Val Ile Ala Val Gln Leu<br>　　　1290　　　　　　　　1295　　　　　　　　1300 | 4000 |
| TTC AAA GGG AAG TTT TTC TAC TGC ACA GAT GAA TCC AAG GAG CTG GAG<br>Phe Lys Gly Lys Phe Phe Tyr Cys Thr Asp Glu Ser Lys Glu Leu Glu<br>　　1305　　　　　　　　1310　　　　　　　　1315 | 4048 |
| AGG GAC TGC AGG GGT CAG TAT TTG GAT TAT GAG AAG GAG GAA GTG GAA<br>Arg Asp Cys Arg Gly Gln Tyr Leu Asp Tyr Glu Lys Glu Glu Val Glu<br>1320　　　　　　　　1325　　　　　　　　1330　　　　　　　　1335 | 4096 |
| GCT CAG CCC AGG CAG TGG AAG AAA TAC GAC TTT CAC TAC GAC AAT GTG<br>Ala Gln Pro Arg Gln Trp Lys Lys Tyr Asp Phe His Tyr Asp Asn Val<br>　　　　　　　　1340　　　　　　　　1345　　　　　　　　1350 | 4144 |
| CTC TGG GCT CTG CTG ACG CTG TTC ACA GTG TCC ACG GGA GAA GGC TGG<br>Leu Trp Ala Leu Leu Thr Leu Phe Thr Val Ser Thr Gly Glu Gly Trp<br>　　　1355　　　　　　　　1360　　　　　　　　1365 | 4192 |
| CCC ATG GTG CTA AAA CAC TCC GTG GAT GCC ACC TAT GAG GAG CAG GGT<br>Pro Met Val Leu Lys His Ser Val Asp Ala Thr Tyr Glu Glu Gln Gly<br>　　1370　　　　　　　　1375　　　　　　　　1380 | 4240 |
| CCA AGC CCT GGG TAC CGC ATG GAG CTG TCC ATC TTC TAC GTG GTC TAC<br>Pro Ser Pro Gly Tyr Arg Met Glu Leu Ser Ile Phe Tyr Val Val Tyr<br>1385　　　　　　　　1390　　　　　　　　1395 | 4288 |
| TTT GTG GTC TTT CCC TTC TTC TTC GTC AAC ATC TTT GTG GCT TTG ATC<br>Phe Val Val Phe Pro Phe Phe Phe Val Asn Ile Phe Val Ala Leu Ile<br>1400　　　　　　　　1405　　　　　　　　1410　　　　　　　　1415 | 4336 |
| ATC ATC ACC TTC CAG GAG CAG GGG GAC AAG GTG ATG TCT GAA TGC AGC<br>Ile Ile Thr Phe Gln Glu Gln Gly Asp Lys Val Met Ser Glu Cys Ser<br>　　　　　　　　1420　　　　　　　　1425　　　　　　　　1430 | 4384 |
| CTG GAG AAG AAC GAG AGG GCT TGC ATT GAC TTC GCC ATC AGC GCC AAA<br>Leu Glu Lys Asn Glu Arg Ala Cys Ile Asp Phe Ala Ile Ser Ala Lys<br>　　　1435　　　　　　　　1440　　　　　　　　1445 | 4432 |
| CCC CTG ACA CGG TAC ATG CCC CAA AAC CGG CAG TCG TTC CAG TAT AAG<br>Pro Leu Thr Arg Tyr Met Pro Gln Asn Arg Gln Ser Phe Gln Tyr Lys<br>　　1450　　　　　　　　1455　　　　　　　　1460 | 4480 |
| ACG TGG ACA TTT GTG GTC TCC CCG CCC TTT GAA TAC TTC ATC ATG GCC<br>Thr Trp Thr Phe Val Val Ser Pro Pro Phe Glu Tyr Phe Ile Met Ala<br>1465　　　　　　　　1470　　　　　　　　1475 | 4528 |
| ATG ATA GCC CTC AAC ACT GTG GTG CTG ATG ATG AAG TTC TAT GAT GCA<br>Met Ile Ala Leu Asn Thr Val Val Leu Met Met Lys Phe Tyr Asp Ala<br>1480　　　　　　　　1485　　　　　　　　1490　　　　　　　　1495 | 4576 |
| CCC TAT GAG TAC GAG CTG ATG CTG AAA TGC CTG AAC ATC GTG TTC ACA<br>Pro Tyr Glu Tyr Glu Leu Met Leu Lys Cys Leu Asn Ile Val Phe Thr<br>　　　　　　　　1500　　　　　　　　1505　　　　　　　　1510 | 4624 |
| TCC ATG TTC TCC ATG GAA TGC GTG CTG AAG ATC ATC GCC TTT GGG GTG<br>Ser Met Phe Ser Met Glu Cys Val Leu Lys Ile Ile Ala Phe Gly Val<br>　　　1515　　　　　　　　1520　　　　　　　　1525 | 4672 |
| CTG AAC TAT TTC AGA GAT GCC TGG AAT GTC TTT GAC TTT GTC ACT GTG<br>Leu Asn Tyr Phe Arg Asp Ala Trp Asn Val Phe Asp Phe Val Thr Val<br>　　1530　　　　　　　　1535　　　　　　　　1540 | 4720 |
| TTG GGA AGT ATT ACT GAT ATT TTA GTA ACA GAG ATT GCG AAC AAT TTC<br>Leu Gly Ser Ile Thr Asp Ile Leu Val Thr Glu Ile Ala Asn Asn Phe<br>1545　　　　　　　　1550　　　　　　　　1555 | 4768 |
| ATC AAC CTC AGC TTC CTC CGC CTC TTT CGA GCT GCG CGG CTG ATC AAG<br>Ile Asn Leu Ser Phe Leu Arg Leu Phe Arg Ala Ala Arg Leu Ile Lys<br>1560　　　　　　　　1565　　　　　　　　1570　　　　　　　　1575 | 4816 |
| CTG CTC CGC CAG GGC TAC ACC ATC CGC ATC CTG CTG TGG ACC TTT GTC<br>Leu Leu Arg Gln Gly Tyr Thr Ile Arg Ile Leu Leu Trp Thr Phe Val<br>　　　　　　　　1580　　　　　　　　1585　　　　　　　　1590 | 4864 |
| CAG TCC TTC AAG GCC CTG CCC TAC GTG TGT CTG CTC ATT GCC ATG CTG<br>Gln Ser Phe Lys Ala Leu Pro Tyr Val Cys Leu Leu Ile Ala Met Leu<br>　　　1595　　　　　　　　1600　　　　　　　　1605 | 4912 |

```
TTC TTC ATC TAC GCC ATC ATC GGC ATG CAG GTG TTT GGG AAT ATT GCC      4960
Phe Phe Ile Tyr Ala Ile Ile Gly Met Gln Val Phe Gly Asn Ile Ala
         1610                1615                1620

CTG GAT GAT GAC ACC AGC ATC AAC CGC CAC AAC AAC TTC CGG ACG TTT      5008
Leu Asp Asp Asp Thr Ser Ile Asn Arg His Asn Asn Phe Arg Thr Phe
1625                1630                1635

TTG CAA GCC CTG ATG CTG CTG TTC AGG AGC GCC ACG GGG GAG GCC TGG      5056
Leu Gln Ala Leu Met Leu Leu Phe Arg Ser Ala Thr Gly Glu Ala Trp
1640                1645                1650                1655

CAC GAG ATC ATG CTG TCC TGC CTG AGC AAC CAG GCC TGT GAT GAG CAG      5104
His Glu Ile Met Leu Ser Cys Leu Ser Asn Gln Ala Cys Asp Glu Gln
             1660                1665                1670

GCC AAT GCC ACC GAG TGT GGA AGT GAC TTT GCC TAC TTC TAC TTC GTC      5152
Ala Asn Ala Thr Glu Cys Gly Ser Asp Phe Ala Tyr Phe Tyr Phe Val
         1675                1680                1685

TCC TTC ATC TTC CTG TGC TCC TTT CTG ATG TTG AAC CTC TTT GTG GCT      5200
Ser Phe Ile Phe Leu Cys Ser Phe Leu Met Leu Asn Leu Phe Val Ala
         1690                1695                1700

GTG ATC ATG GAC AAT TTT GAG TAC CTC ACG CGG GAC TCT TCC ATC CTA      5248
Val Ile Met Asp Asn Phe Glu Tyr Leu Thr Arg Asp Ser Ser Ile Leu
     1705                1710                1715

GGT CCT CAC CAC TTG GAT GAG TTC ATC CGG GTC TGG GCT GAA TAC GAC      5296
Gly Pro His His Leu Asp Glu Phe Ile Arg Val Trp Ala Glu Tyr Asp
1720                1725                1730                1735

CCG GCT GCG TGT GGG CGC ATC AGT TAC AAT GAC ATG TTT GAG ATG CTG      5344
Pro Ala Ala Cys Gly Arg Ile Ser Tyr Asn Asp Met Phe Glu Met Leu
             1740                1745                1750

AAA CAC ATG TCC CCG CCT CTG GGG CTG GGG AAG AAA TGC CCT GCT CGA      5392
Lys His Met Ser Pro Pro Leu Gly Leu Gly Lys Lys Cys Pro Ala Arg
         1755                1760                1765

GTT GCT TAC AAG CGC CTG GTT CGC ATG AAC ATG CCC ATC TCC AAC GAG      5440
Val Ala Tyr Lys Arg Leu Val Arg Met Asn Met Pro Ile Ser Asn Glu
         1770                1775                1780

GAC ATG ACT GTT CAC TTC ACG TCC ACG CTG ATG GCC CTC ATC CGG ACG      5488
Asp Met Thr Val His Phe Thr Ser Thr Leu Met Ala Leu Ile Arg Thr
         1785                1790                1795

GCA CTG GAG ATC AAG CTG GCC CCA GCT GGG ACA AAG CAG CAT CAG TGT      5536
Ala Leu Glu Ile Lys Leu Ala Pro Ala Gly Thr Lys Gln His Gln Cys
1800                1805                1810                1815

GAC GCG GAG TTG AGG AAG GAG ATT TCC GTT GTG TGG GCC AAT CTG CCC      5584
Asp Ala Glu Leu Arg Lys Glu Ile Ser Val Val Trp Ala Asn Leu Pro
             1820                1825                1830

CAG AAG ACT TTG GAC TTG CTG GTA CCA CCC CAT AAG CCT GAT GAG ATG      5632
Gln Lys Thr Leu Asp Leu Leu Val Pro Pro His Lys Pro Asp Glu Met
         1835                1840                1845

ACA GTG GGG AAG GTT TAT GCA GCT CTG ATG ATA TTT GAC TTC TAC AAG      5680
Thr Val Gly Lys Val Tyr Ala Ala Leu Met Ile Phe Asp Phe Tyr Lys
         1850                1855                1860

CAG AAC AAA ACC ACC AGA GAC CAG ATG CAG CAG GCT CCT GGA GGC CTC      5728
Gln Asn Lys Thr Thr Arg Asp Gln Met Gln Gln Ala Pro Gly Gly Leu
         1865                1870                1875

TCC CAG ATG GGT CCT GTG TCC CTG TTC CAC CCT CTG AAG GCC ACC CTG      5776
Ser Gln Met Gly Pro Val Ser Leu Phe His Pro Leu Lys Ala Thr Leu
1880                1885                1890                1895

GAG CAG ACA CAG CCG GCT GTG CTC CGA GGA GCC CGG GTT TTC CTT CGA      5824
Glu Gln Thr Gln Pro Ala Val Leu Arg Gly Ala Arg Val Phe Leu Arg
         1900                1905                1910
```

```
CAG AAG AGT TCC ACC TCC CTC AGC AAT GGC GGG GCC ATA CAA AAC CAA      5872
Gln Lys Ser Ser Thr Ser Leu Ser Asn Gly Gly Ala Ile Gln Asn Gln
            1915                1920                1925

GAG AGT GGC ATC AAA GAG TCT GTC TCC TGG GGC ACT CAA AGG ACC CAG      5920
Glu Ser Gly Ile Lys Glu Ser Val Ser Trp Gly Thr Gln Arg Thr Gln
        1930                1935                1940

GAT GCA CCC CAT GAG GCC AGG CCA CCC CTG GAG CGT GGC CAC TCC ACA      5968
Asp Ala Pro His Glu Ala Arg Pro Pro Leu Glu Arg Gly His Ser Thr
    1945                1950                1955

GAG ATC CCT GTG GGG CGG TCA GGA GCA CTG GCT GTG GAC GTT CAG ATG      6016
Glu Ile Pro Val Gly Arg Ser Gly Ala Leu Ala Val Asp Val Gln Met
1960                1965                1970                1975

CAG AGC ATA ACC CGG AGG GGC CCT GAT GGG GAG CCC CAG CCT GGG CTG      6064
Gln Ser Ile Thr Arg Arg Gly Pro Asp Gly Glu Pro Gln Pro Gly Leu
                1980                1985                1990

GAG AGC CAG GGT CGA GCG GCC TCC ATG CCC CGC CTT GCG GCC GAG ACT      6112
Glu Ser Gln Gly Arg Ala Ala Ser Met Pro Arg Leu Ala Ala Glu Thr
            1995                2000                2005

CAG CCC GTC ACA GAT GCC AGC CCC ATG AAG CGC TCC ATC TCC ACG CTG      6160
Gln Pro Val Thr Asp Ala Ser Pro Met Lys Arg Ser Ile Ser Thr Leu
        2010                2015                2020

GCC CAG CGG CCC CGT GGG ACT CAT CTT TGC AGC ACC ACC CCG GAC CGC      6208
Ala Gln Arg Pro Arg Gly Thr His Leu Cys Ser Thr Thr Pro Asp Arg
    2025                2030                2035

CCA CCC CCT AGC CAG GCG TCG TCG CAC CAC CAC CAC CAC CGC TGC CAC      6256
Pro Pro Pro Ser Gln Ala Ser Ser His His His His His Arg Cys His
2040                2045                2050                2055

CGC CGC AGG GAC AGG AAG CAG AGG TCC CTG GAG AAG GGG CCC AGC CTG      6304
Arg Arg Arg Asp Arg Lys Gln Arg Ser Leu Glu Lys Gly Pro Ser Leu
                2060                2065                2070

TCT GCC GAT ATG GAT GGC GCA CCA AGC AGT GCT GTG GGG CCG GGG CTG      6352
Ser Ala Asp Met Asp Gly Ala Pro Ser Ser Ala Val Gly Pro Gly Leu
            2075                2080                2085

CCC CCG GGA GAG GGG CCT ACA GGC TGC CGG CGG GAA CGA GAG CGC CGG      6400
Pro Pro Gly Glu Gly Pro Thr Gly Cys Arg Arg Glu Arg Glu Arg Arg
        2090                2095                2100

CAG GAG CGG AGC CGG TCC CAG GAG CGG AGG CAG CCC TCA TCC TCC TCC      6448
Gln Glu Arg Ser Arg Ser Gln Glu Arg Arg Gln Pro Ser Ser Ser Ser
    2105                2110                2115

TCG GAG AAG CAG CGC TTC TAC TCC TGC GAC CGC TTT GGG GGC CGT GAG      6496
Ser Glu Lys Gln Arg Phe Tyr Ser Cys Asp Arg Phe Gly Gly Arg Glu
2120                2125                2130                2135

CCC CCG AAG CCC AAG CCC TCC CTC AGC AGC CAC CCA ACG TCG CCA ACA      6544
Pro Pro Lys Pro Lys Pro Ser Leu Ser Ser His Pro Thr Ser Pro Thr
                2140                2145                2150

GCT GGC CAG GAG CCG GGA CCC CAC CCA CAG GGC AGT GGT TCC GTG AAT      6592
Ala Gly Gln Glu Pro Gly Pro His Pro Gln Gly Ser Gly Ser Val Asn
            2155                2160                2165

GGG AGC CCC TTG CTG TCA ACA TCT GGT GCT AGC ACC CCC GGC CGC GGT      6640
Gly Ser Pro Leu Leu Ser Thr Ser Gly Ala Ser Thr Pro Gly Arg Gly
        2170                2175                2180

GGG CGG AGG CAG CTC CCC CAG ACG CCC CTG ACT CCC CGC CCC AGC ATC      6688
Gly Arg Arg Gln Leu Pro Gln Thr Pro Leu Thr Pro Arg Pro Ser Ile
    2185                2190                2195

ACC TAC AAG ACG GCC AAC TCC TCA CCC ATC CAC TTC GCC GGG GCT CAG      6736
Thr Tyr Lys Thr Ala Asn Ser Ser Pro Ile His Phe Ala Gly Ala Gln
2200                2205                2210                2215

ACC AGC CTC CCT GCC TTC TCC CCA GGC CGG CTC AGC CGT GGG CTT TCC      6784
Thr Ser Leu Pro Ala Phe Ser Pro Gly Arg Leu Ser Arg Gly Leu Ser
                2220                2225                2230
```

```
GAA CAC AAC GCC CTG CTG CAG AGA GAC CCC CTC AGC CAG CCC CTG GCC    6832
Glu His Asn Ala Leu Leu Gln Arg Asp Pro Leu Ser Gln Pro Leu Ala
            2235                2240                2245

CCT GGC TCT CGA ATT GGC TCT GAC CCT TAC CTG GGG CAG CGT CTG GAC    6880
Pro Gly Ser Arg Ile Gly Ser Asp Pro Tyr Leu Gly Gln Arg Leu Asp
            2250                2255                2260

AGT GAG GCC TCT GTC CAC GCC CTG CCT GAG GAC ACG CTC ACT TTC GAG    6928
Ser Glu Ala Ser Val His Ala Leu Pro Glu Asp Thr Leu Thr Phe Glu
            2265                2270                2275

GAG GCT GTG GCC ACC AAC TCG GGC CGC TCC TCC AGG ACT TCC TAC GTG    6976
Glu Ala Val Ala Thr Asn Ser Gly Arg Ser Ser Arg Thr Ser Tyr Val
2280                2285                2290                2295

TCC TCC CTG ACC TCC CAG TCT CAC CCT CTC CGC CGC GTG CCC AAC GGT    7024
Ser Ser Leu Thr Ser Gln Ser His Pro Leu Arg Arg Val Pro Asn Gly
                2300                2305                2310

TAC CAC TGC ACC CTG GGA CTC AGC TCG GGT GGC CGA GCA CGG CAC AGC    7072
Tyr His Cys Thr Leu Gly Leu Ser Ser Gly Gly Arg Ala Arg His Ser
                2315                2320                2325

TAC CAC CAC CCT GAC CAA GAC CAC TGG TGC TAGCTGCACC GTGACCGCTC      7122
Tyr His His Pro Asp Gln Asp His Trp Cys
            2330                2335

AGACGCCTGC ATGCAGCAGG CGTGTGTTCC AGTGGATGAG TTTTATCATC CACACGGGGC  7182

AGTCGGCCCT CGGGGGAGGC CTTGCCCACC TTGGTGAGGC TCCTGTGGCC CCTCCCTCCC  7242

CCTCCTCCCC TCTTTTACTC TAGA                                        7266

(2) INFORMATION FOR SEQ ID NO:2:

(i) SEQUENCE CHARACTERISTICS:
        (A) LENGTH: 2337 amino acids
        (B) TYPE: amino acid
        (D) TOPOLOGY: linear (ii) MOLECULE TYPE: protein (xi) SEQUENCE DESCRIPTION: SEQ ID NO:2:

Met Val Arg Phe Gly Asp Glu Leu Gly Gly Arg Tyr Gly Gly Pro Gly
 1               5                  10                  15

Ser Gly Glu Arg Ala Arg Gly Gly Ala Gly Gly Ala Gly Gly Pro
            20                  25                  30

Gly Pro Gly Gly Leu Gln Pro Gly Gln Arg Val Leu Tyr Lys Gln Ser
            35                  40                  45

Ile Ala Gln Arg Ala Arg Thr Met Ala Leu Tyr Asn Pro Ile Pro Val
        50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
                100                 105                 110

Ala Leu Glu Gln His Leu Pro Asp Gly Asp Lys Thr Pro Met Ser Glu
            115                 120                 125

Arg Leu Asp Asp Thr Glu Pro Tyr Phe Ile Gly Ile Phe Cys Phe Glu
        130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Leu Thr
                165                 170                 175
```

-continued

```
Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
            245                 250                 255

Ser Thr Asp Ala Glu Pro Val Gly Asp Phe Pro Cys Gly Lys Glu Ala
        260                 265                 270

Pro Ala Arg Leu Cys Glu Gly Asp Thr Glu Cys Arg Glu Tyr Trp Pro
    275                 280                 285

Gly Pro Asn Phe Gly Ile Thr Asn Phe Asp Asn Ile Leu Phe Ala Ile
            290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
            325                 330                 335

Ile Pro Leu Ile Ile Ile Gly Ser Phe Phe Met Leu Asn Leu Val Leu
        340                 345                 350

Gly Val Leu Ser Gly Glu Phe Ala Lys Glu Arg Glu Arg Val Glu Asn
            355                 360                 365

Arg Arg Ala Phe Leu Lys Leu Arg Arg Gln Gln Gln Ile Glu Arg Glu
370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
            405                 410                 415

Lys Arg Ala Ala Thr Lys Lys Ser Arg Asn Asp Leu Ile His Ala Glu
        420                 425                 430

Glu Gly Glu Asp Arg Phe Ala Asp Leu Cys Ala Val Gly Ser Pro Phe
    435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
            485                 490                 495

Leu Cys Val Ala Met Val His Tyr Asn Gln Pro Arg Arg Leu Thr Thr
        500                 505                 510

Thr Leu Tyr Phe Ala Glu Phe Val Phe Leu Gly Leu Phe Leu Thr Glu
    515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Val Phe Glu
545                 550                 555                 560

Val Val Trp Ala Ala Ile Lys Pro Gly Ser Ser Phe Gly Ile Ser Val
            565                 570                 575

Leu Arg Ala Leu Arg Leu Leu Arg Ile Phe Lys Val Thr Lys Tyr Trp
        580                 585                 590
```

-continued

```
Ser Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685

Phe Ile Val Leu Thr Leu Phe Gly Asn Tyr Thr Leu Leu Asn Val Phe
690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765

Glu Gln Arg Ala Ser Gln Leu Arg Leu Gln Asn Leu Arg Ala Ser Cys
770                 775                 780

Glu Ala Leu Tyr Ser Glu Met Asp Pro Glu Glu Arg Leu Arg Phe Ala
785                 790                 795                 800

Thr Thr Arg His Arg Arg Pro Asp Met Lys Thr His Leu Asp Arg Pro
                805                 810                 815

Leu Val Val Glu Leu Gly Arg Asp Gly Ala Arg Gly Pro Val Gly Gly
            820                 825                 830

Lys Ala Arg Pro Glu Ala Ala Glu Ala Pro Glu Gly Val Asp Pro Pro
        835                 840                 845

Arg Arg His His Arg His Arg Asp Lys Asp Lys Thr Pro Ala Ala Gly
850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
                885                 890                 895

Ala Gly Pro Pro Glu Ala Arg Ser Glu Arg Gly Arg Gly Pro Gly Pro
            900                 905                 910

Glu Gly Gly Arg Arg His His Arg Arg Gly Ser Pro Glu Glu Ala Ala
        915                 920                 925

Glu Arg Glu Pro Arg Arg His Arg Ala His Arg His Gln Asp Pro Ser
930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
                965                 970                 975

Arg Arg His Arg Ala Arg His Lys Ala Gln Pro Ala His Glu Ala Val
            980                 985                 990

Glu Lys Glu Thr Thr Glu Lys Glu Ala Thr Glu Lys Glu Ala Glu Ile
        995                 1000                1005
```

Val Glu Ala Asp Lys Glu Lys Glu Leu Arg Asn His Gln Pro Arg Glu
    1010                1015                1020

Pro His Cys Asp Leu Glu Thr Ser Gly Thr Val Thr Val Gly Pro Met
1025                1030                1035                1040

His Thr Leu Pro Ser Thr Cys Leu Gln Lys Val Glu Gln Pro Glu
                1045                1050                1055

Asp Ala Asp Asn Gln Arg Asn Val Thr Arg Met Gly Ser Gln Pro Pro
            1060                1065                1070

Asp Pro Asn Thr Ile Val His Ile Pro Val Met Leu Thr Gly Pro Leu
        1075                1080                1085

Gly Glu Ala Thr Val Val Pro Ser Gly Asn Val Asp Leu Glu Ser Gln
        1090                1095                1100

Ala Glu Gly Lys Lys Glu Val Glu Ala Asp Asp Val Met Arg Ser Gly
1105                1110                1115                1120

Pro Arg Pro Ile Val Pro Tyr Ser Ser Met Phe Cys Leu Ser Pro Thr
                1125                1130                1135

Asn Leu Leu Arg Arg Phe Cys His Tyr Ile Val Thr Met Arg Tyr Phe
            1140                1145                1150

Glu Val Val Ile Leu Val Val Ile Ala Leu Ser Ser Ile Ala Leu Ala
        1155                1160                1165

Ala Glu Asp Pro Val Arg Thr Asp Ser Pro Arg Asn Asn Ala Leu Lys
    1170                1175                1180

Tyr Leu Asp Tyr Ile Phe Thr Gly Val Phe Thr Phe Glu Met Val Ile
1185                1190                1195                1200

Lys Met Ile Asp Leu Gly Leu Leu His Pro Gly Ala Tyr Phe Arg
                1205                1210                1215

Asp Leu Trp Asn Ile Leu Asp Phe Ile Val Val Ser Gly Ala Leu Val
            1220                1225                1230

Ala Phe Ala Phe Ser Gly Ser Lys Gly Lys Asp Ile Asn Thr Ile Lys
        1235                1240                1245

Ser Leu Arg Val Leu Arg Val Leu Arg Pro Leu Lys Thr Ile Lys Arg
    1250                1255                1260

Leu Pro Lys Leu Lys Ala Val Phe Asp Cys Val Val Asn Ser Leu Lys
1265                1270                1275                1280

Asn Val Leu Asn Ile Leu Ile Val Tyr Met Leu Phe Met Phe Ile Phe
                1285                1290                1295

Ala Val Ile Ala Val Gln Leu Phe Lys Gly Lys Phe Phe Tyr Cys Thr
            1300                1305                1310

Asp Glu Ser Lys Glu Leu Glu Arg Asp Cys Arg Gly Gln Tyr Leu Asp
        1315                1320                1325

Tyr Glu Lys Glu Glu Val Glu Ala Gln Pro Arg Gln Trp Lys Lys Tyr
    1330                1335                1340

Asp Phe His Tyr Asp Asn Val Leu Trp Ala Leu Leu Thr Leu Phe Thr
1345                1350                1355                1360

Val Ser Thr Gly Glu Gly Trp Pro Met Val Leu Lys His Ser Val Asp
                1365                1370                1375

Ala Thr Tyr Glu Glu Gln Gly Pro Ser Pro Gly Tyr Arg Met Glu Leu
            1380                1385                1390

Ser Ile Phe Tyr Val Val Tyr Phe Val Val Phe Pro Phe Phe Phe Val
        1395                1400                1405

Asn Ile Phe Val Ala Leu Ile Ile Ile Thr Phe Gln Glu Gln Gly Asp
    1410                1415                1420

-continued

```
Lys Val Met Ser Glu Cys Ser Leu Glu Lys Asn Glu Arg Ala Cys Ile
1425                1430                1435                1440

Asp Phe Ala Ile Ser Ala Lys Pro Leu Thr Arg Tyr Met Pro Gln Asn
            1445                1450                1455

Arg Gln Ser Phe Gln Tyr Lys Thr Trp Thr Phe Val Val Ser Pro Pro
            1460                1465                1470

Phe Glu Tyr Phe Ile Met Ala Met Ile Ala Leu Asn Thr Val Val Leu
            1475                1480                1485

Met Met Lys Phe Tyr Asp Ala Pro Tyr Glu Tyr Glu Leu Met Leu Lys
            1490                1495                1500

Cys Leu Asn Ile Val Phe Thr Ser Met Phe Ser Met Glu Cys Val Leu
1505                1510                1515                1520

Lys Ile Ile Ala Phe Gly Val Leu Asn Tyr Phe Arg Asp Ala Trp Asn
            1525                1530                1535

Val Phe Asp Phe Val Thr Val Leu Gly Ser Ile Thr Asp Ile Leu Val
            1540                1545                1550

Thr Glu Ile Ala Asn Asn Phe Ile Asn Leu Ser Phe Leu Arg Leu Phe
            1555                1560                1565

Arg Ala Ala Arg Leu Ile Lys Leu Leu Arg Gln Gly Tyr Thr Ile Arg
            1570                1575                1580

Ile Leu Leu Trp Thr Phe Val Gln Ser Phe Lys Ala Leu Pro Tyr Val
1585                1590                1595                1600

Cys Leu Leu Ile Ala Met Leu Phe Phe Ile Tyr Ala Ile Ile Gly Met
            1605                1610                1615

Gln Val Phe Gly Asn Ile Ala Leu Asp Asp Asp Thr Ser Ile Asn Arg
            1620                1625                1630

His Asn Asn Phe Arg Thr Phe Leu Gln Ala Leu Met Leu Leu Phe Arg
            1635                1640                1645

Ser Ala Thr Gly Glu Ala Trp His Glu Ile Met Leu Ser Cys Leu Ser
            1650                1655                1660

Asn Gln Ala Cys Asp Glu Gln Ala Asn Ala Thr Glu Cys Gly Ser Asp
1665                1670                1675                1680

Phe Ala Tyr Phe Tyr Phe Val Ser Phe Ile Phe Leu Cys Ser Phe Leu
            1685                1690                1695

Met Leu Asn Leu Phe Val Ala Val Ile Met Asp Asn Phe Glu Tyr Leu
            1700                1705                1710

Thr Arg Asp Ser Ser Ile Leu Gly Pro His His Leu Asp Glu Phe Ile
            1715                1720                1725

Arg Val Trp Ala Glu Tyr Asp Pro Ala Ala Cys Gly Arg Ile Ser Tyr
            1730                1735                1740

Asn Asp Met Phe Glu Met Leu Lys His Met Ser Pro Pro Leu Gly Leu
1745                1750                1755                1760

Gly Lys Lys Cys Pro Ala Arg Val Ala Tyr Lys Arg Leu Val Arg Met
            1765                1770                1775

Asn Met Pro Ile Ser Asn Glu Asp Met Thr Val His Phe Thr Ser Thr
            1780                1785                1790

Leu Met Ala Leu Ile Arg Thr Ala Leu Glu Ile Lys Leu Ala Pro Ala
            1795                1800                1805

Gly Thr Lys Gln His Gln Cys Asp Ala Glu Leu Arg Lys Glu Ile Ser
            1810                1815                1820

Val Val Trp Ala Asn Leu Pro Gln Lys Thr Leu Asp Leu Leu Val Pro
1825                1830                1835                1840
```

-continued

```
Pro His Lys Pro Asp Glu Met Thr Val Gly Lys Val Tyr Ala Ala Leu
            1845                1850                1855
Met Ile Phe Asp Phe Tyr Lys Gln Asn Lys Thr Thr Arg Asp Gln Met
            1860                1865                1870
Gln Gln Ala Pro Gly Gly Leu Ser Gln Met Gly Pro Val Ser Leu Phe
            1875                1880                1885
His Pro Leu Lys Ala Thr Leu Gln Thr Gln Pro Ala Val Leu Arg
            1890                1895            1900
Gly Ala Arg Val Phe Leu Arg Gln Lys Ser Ser Thr Ser Leu Ser Asn
1905                1910                1915                1920
Gly Gly Ala Ile Gln Asn Gln Glu Ser Gly Ile Lys Glu Ser Val Ser
                1925                1930                1935
Trp Gly Thr Gln Arg Thr Gln Asp Ala Pro His Glu Ala Arg Pro Pro
            1940                1945                1950
Leu Glu Arg Gly His Ser Thr Glu Ile Pro Val Gly Arg Ser Gly Ala
            1955                1960                1965
Leu Ala Val Asp Val Gln Met Gln Ser Ile Thr Arg Arg Gly Pro Asp
            1970                1975                1980
Gly Glu Pro Gln Pro Gly Leu Glu Ser Gln Gly Arg Ala Ala Ser Met
1985                1990                1995                2000
Pro Arg Leu Ala Ala Glu Thr Gln Pro Val Thr Asp Ala Ser Pro Met
            2005                2010                2015
Lys Arg Ser Ile Ser Thr Leu Ala Gln Arg Pro Arg Gly Thr His Leu
            2020                2025                2030
Cys Ser Thr Thr Pro Asp Arg Pro Pro Ser Gln Ala Ser Ser His
            2035                2040                2045
His His His His Arg Cys His Arg Arg Asp Arg Lys Gln Arg Ser
            2050                2055                2060
Leu Glu Lys Gly Pro Ser Leu Ser Ala Asp Met Asp Gly Ala Pro Ser
2065                2070                2075                2080
Ser Ala Val Gly Pro Gly Leu Pro Pro Gly Glu Gly Pro Thr Gly Cys
            2085                2090                2095
Arg Arg Glu Arg Glu Arg Gln Glu Arg Ser Arg Ser Gln Glu Arg
            2100                2105                2110
Arg Gln Pro Ser Ser Ser Ser Glu Lys Gln Arg Phe Tyr Ser Cys
            2115                2120                2125
Asp Arg Phe Gly Arg Glu Pro Pro Lys Pro Lys Pro Ser Leu Ser
            2130                2135                2140
Ser His Pro Thr Ser Pro Thr Ala Gly Gln Glu Pro Gly Pro His Pro
2145                2150                2155                2160
Gln Gly Ser Gly Ser Val Asn Gly Ser Pro Leu Leu Ser Thr Ser Gly
                2165                2170                2175
Ala Ser Thr Pro Gly Arg Gly Gly Arg Arg Gln Leu Pro Gln Thr Pro
            2180                2185                2190
Leu Thr Pro Arg Pro Ser Ile Thr Tyr Lys Thr Ala Asn Ser Ser Pro
            2195                2200                2205
Ile His Phe Ala Gly Ala Gln Thr Ser Leu Pro Ala Phe Ser Pro Gly
            2210                2215                2220
Arg Leu Ser Arg Gly Leu Ser Glu His Asn Ala Leu Leu Gln Arg Asp
2225                2230                2235                2240
Pro Leu Ser Gln Pro Leu Ala Pro Gly Ser Arg Ile Gly Ser Asp Pro
            2245                2250                2255
```

```
Tyr Leu Gly Gln Arg Leu Asp Ser Glu Ala Ser Val His Ala Leu Pro
        2260                2265                2270

Glu Asp Thr Leu Thr Phe Glu Glu Ala Val Ala Thr Asn Ser Gly Arg
    2275                2280                2285

Ser Ser Arg Thr Ser Tyr Val Ser Ser Leu Thr Ser Gln Ser His Pro
2290                2295                2300

Leu Arg Arg Val Pro Asn Gly Tyr His Cys Thr Leu Gly Leu Ser Ser
2305                2310                2315                2320

Gly Gly Arg Ala Arg His Ser Tyr His His Pro Asp Gln Asp His Trp
            2325                2330                2335

Cys (2) INFORMATION FOR SEQ ID NO:3:

(i) SEQUENCE CHARACTERISTICS:
        (A) LENGTH: 3298 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 20..3292

(xi) SEQUENCE DESCRIPTION: SEQ ID NO:3:

TTGATCTTCG ATCGCGAAG ATG GCT GCT GGC TGC CTG CTG GCC TTG ACT CTG         52
                    Met Ala Ala Gly Cys Leu Leu Ala Leu Thr Leu
                        2340                2345

ACA CTT TTC CAA TCT TTG CTC ATC GGC CCC TCG TCG GAG GAG CCG TTC        100
Thr Leu Phe Gln Ser Leu Leu Ile Gly Pro Ser Ser Glu Glu Pro Phe
    2350                2355                2360

CCT TCG GCC GTC ACT ATC AAA TCA TGG GTG GAT AAG ATG CAA GAA GAC        148
Pro Ser Ala Val Thr Ile Lys Ser Trp Val Asp Lys Met Gln Glu Asp
2365                2370                2375                2380

CTT GTC ACA CTG GCA AAA ACA GCA AGT GGA GTC AAT CAG CTT GTT GAT        196
Leu Val Thr Leu Ala Lys Thr Ala Ser Gly Val Asn Gln Leu Val Asp
            2385                2390                2395

ATT TAT GAG AAA TAT CAA GAT TTG TAT ACT GTG GAA CCA AAT AAT GCA        244
Ile Tyr Glu Lys Tyr Gln Asp Leu Tyr Thr Val Glu Pro Asn Asn Ala
        2400                2405                2410

CGC CAG CTG GTA GAA ATT GCA GCC AGG GAT ATT GAG AAA CTT CTG AGC        292
Arg Gln Leu Val Glu Ile Ala Ala Arg Asp Ile Glu Lys Leu Leu Ser
    2415                2420                2425

AAC AGA TCT AAA GCC CTG GTG AGC CTG GCA TTG GAA GCG GAG AAA GTT        340
Asn Arg Ser Lys Ala Leu Val Ser Leu Ala Leu Glu Ala Glu Lys Val
    2430                2435                2440

CAA GCA GCT CAC CAG TGG AGA GAA GAT TTT GCA AGC AAT GAA GTT GTC        388
Gln Ala Ala His Gln Trp Arg Glu Asp Phe Ala Ser Asn Glu Val Val
2445                2450                2455                2460

TAC TAC AAT GCA AAG GAT GAT CTC GAT CCT GAG AAA AAT GAC AGT GAG        436
Tyr Tyr Asn Ala Lys Asp Asp Leu Asp Pro Glu Lys Asn Asp Ser Glu
            2465                2470                2475

CCA GGC AGC CAG AGG ATA AAA CCT GTT TTC ATT GAA GAT GCT AAT TTT        484
Pro Gly Ser Gln Arg Ile Lys Pro Val Phe Ile Glu Asp Ala Asn Phe
        2480                2485                2490

GGA CGA CAA ATA TCT TAT CAG CAC GCA GCA GTC CAT ATT CCT ACT GAC        532
Gly Arg Gln Ile Ser Tyr Gln His Ala Ala Val His Ile Pro Thr Asp
    2495                2500                2505
```

```
ATC TAT GAG GGC TCA ACA ATT GTG TTA AAT GAA CTC AAC TGG ACA AGT         580
Ile Tyr Glu Gly Ser Thr Ile Val Leu Asn Glu Leu Asn Trp Thr Ser
    2510            2515                2520

GCC TTA GAT GAA GTT TTC AAA AAG AAT CGC GAG GAA GAC CCT TCA TTA         628
Ala Leu Asp Glu Val Phe Lys Lys Asn Arg Glu Glu Asp Pro Ser Leu
2525            2530                2535                2540

TTG TGG CAG GTT TTT GGC AGT GCC ACT GGC CTA GCT CGA TAT TAT CCA         676
Leu Trp Gln Val Phe Gly Ser Ala Thr Gly Leu Ala Arg Tyr Tyr Pro
            2545                2550                2555

GCT TCA CCA TGG GTT GAT AAT AGT AGA ACT CCA AAT AAG ATT GAC CTT         724
Ala Ser Pro Trp Val Asp Asn Ser Arg Thr Pro Asn Lys Ile Asp Leu
        2560                2565                2570

TAT GAT GTA CGC AGA AGA CCA TGG TAC ATC CAA GGA GCT GCA TCT CCT         772
Tyr Asp Val Arg Arg Arg Pro Trp Tyr Ile Gln Gly Ala Ala Ser Pro
    2575                2580                2585

AAA GAC ATG CTT ATT CTG GTG GAT GTG AGT GGA AGT GTT AGT GGA TTG         820
Lys Asp Met Leu Ile Leu Val Asp Val Ser Gly Ser Val Ser Gly Leu
            2590                2595                2600

ACA CTT AAA CTG ATC CGA ACA TCT GTC TCC GAA ATG TTA GAA ACC CTC         868
Thr Leu Lys Leu Ile Arg Thr Ser Val Ser Glu Met Leu Glu Thr Leu
2605            2610                2615                2620

TCA GAT GAT GAT TTC GTG AAT GTA GCT TCA TTT AAC AGC AAT GCT CAG         916
Ser Asp Asp Asp Phe Val Asn Val Ala Ser Phe Asn Ser Asn Ala Gln
            2625                2630                2635

GAT GTA AGC TGT TTT CAG CAC CTT GTC CAA GCA AAT GTA AGA AAT AAA         964
Asp Val Ser Cys Phe Gln His Leu Val Gln Ala Asn Val Arg Asn Lys
        2640                2645                2650

AAA GTG TTG AAA GAC GCG GTG AAT AAT ATC ACA GCC AAA GGA ATT ACA        1012
Lys Val Leu Lys Asp Ala Val Asn Asn Ile Thr Ala Lys Gly Ile Thr
    2655                2660                2665

GAT TAT AAG AAG GGC TTT AGT TTT GCT TTT GAA CAG CTG CTT AAT TAT        1060
Asp Tyr Lys Lys Gly Phe Ser Phe Ala Phe Glu Gln Leu Leu Asn Tyr
2670            2675                2680

AAT GTT TCC AGA GCA AAC TGC AAT AAG ATT ATT ATG CTA TTC ACG GAT        1108
Asn Val Ser Arg Ala Asn Cys Asn Lys Ile Ile Met Leu Phe Thr Asp
2685            2690                2695                2700

GGA GGA GAA GAG AGA GCC CAG GAG ATA TTT AAC AAA TAC AAT AAA GAT        1156
Gly Gly Glu Glu Arg Ala Gln Glu Ile Phe Asn Lys Tyr Asn Lys Asp
            2705                2710                2715

AAA AAA GTA CGT GTA TTC AGG TTT TCA GTT GGT CAA CAC AAT TAT GAG        1204
Lys Lys Val Arg Val Phe Arg Phe Ser Val Gly Gln His Asn Tyr Glu
        2720                2725                2730

AGA GGA CCT ATT CAG TGG ATG GCC TGT GAA AAC AAA GGT TAT TAT TAT        1252
Arg Gly Pro Ile Gln Trp Met Ala Cys Glu Asn Lys Gly Tyr Tyr Tyr
    2735                2740                2745

GAA ATT CCT TCC ATT GGT GCA ATA AGA ATC AAT ACT CAG GAA TAT TTG        1300
Glu Ile Pro Ser Ile Gly Ala Ile Arg Ile Asn Thr Gln Glu Tyr Leu
2750            2755                2760

GAT GTT TTG GGA AGA CCA ATG GTT TTA GCA GGA GAC AAA GCT AAG CAA        1348
Asp Val Leu Gly Arg Pro Met Val Leu Ala Gly Asp Lys Ala Lys Gln
2765            2770                2775                2780

GTC CAA TGG ACA AAT GTG TAC CTG GAT GCA TTG GAA CTG GGA CTT GTC        1396
Val Gln Trp Thr Asn Val Tyr Leu Asp Ala Leu Glu Leu Gly Leu Val
            2785                2790                2795

ATT ACT GGA ACT CTT CCG GTC TTC AAC ATA ACC GGC CAA TTT GAA AAT        1444
Ile Thr Gly Thr Leu Pro Val Phe Asn Ile Thr Gly Gln Phe Glu Asn
        2800                2805                2810

AAG ACA AAC TTA AAG AAC CAG CTG ATT CTT GGT GTG ATG GGA GTA GAT        1492
Lys Thr Asn Leu Lys Asn Gln Leu Ile Leu Gly Val Met Gly Val Asp
    2815                2820                2825
```

```
GTG TCT TTG GAA GAT ATT AAA AGA CTG ACA CCA CGT TTT ACA CTG TGC      1540
Val Ser Leu Glu Asp Ile Lys Arg Leu Thr Pro Arg Phe Thr Leu Cys
        2830                2835                2840

CCC AAT GGG TAT TAC TTT GCA ATC GAT CCT AAT GGT TAT GCT TTA TTA      1588
Pro Asn Gly Tyr Tyr Phe Ala Ile Asp Pro Asn Gly Tyr Ala Leu Leu
2845                2850                2855                2860

CAT CCA AAT CTT CAG CCA AAG AAC CCC AAA TCT CAG GAG CCA GTA ACA      1636
His Pro Asn Leu Gln Pro Lys Asn Pro Lys Ser Gln Glu Pro Val Thr
                2865                2870                2875

TTG GAT TTC CTT GAT GCA GAG TTA GAG AAT GAT ATT AAA GTG GAG ATT      1684
Leu Asp Phe Leu Asp Ala Glu Leu Glu Asn Asp Ile Lys Val Glu Ile
            2880                2885                2890

CGA AAT AAG ATG ATT GAT GGG GAA AGT GGA GAA AAA ACA TTC AGA ACT      1732
Arg Asn Lys Met Ile Asp Gly Glu Ser Gly Glu Lys Thr Phe Arg Thr
        2895                2900                2905

CTG GTT AAA TCT CAA GAT GAG AGA TAT ATT GAC AAA GGA AAC AGG ACA      1780
Leu Val Lys Ser Gln Asp Glu Arg Tyr Ile Asp Lys Gly Asn Arg Thr
    2910                2915                2920

TAC ACA TGG ACA CCT GTC AAT GGC ACA GAT TAC AGT TTG GCC TTG GTA      1828
Tyr Thr Trp Thr Pro Val Asn Gly Thr Asp Tyr Ser Leu Ala Leu Val
2925                2930                2935                2940

TTA CCA ACC TAC AGT TTT TAC TAT ATA AAA GCC AAA CTA GAA GAG ACA      1876
Leu Pro Thr Tyr Ser Phe Tyr Tyr Ile Lys Ala Lys Leu Glu Glu Thr
                2945                2950                2955

ATA ACT CAG GCC AGA TCA AAA AAG GGC AAA ATG AAG GAT TCG GAA ACC      1924
Ile Thr Gln Ala Arg Ser Lys Lys Gly Lys Met Lys Asp Ser Glu Thr
            2960                2965                2970

CTG AAG CCA GAT AAT TTT GAA GAA TCT GGC TAT ACA TTC ATA GCA CCA      1972
Leu Lys Pro Asp Asn Phe Glu Glu Ser Gly Tyr Thr Phe Ile Ala Pro
        2975                2980                2985

AGA GAT TAC TGC AAT GAC CTG AAA ATA TCG GAT AAT AAC ACT GAA TTT      2020
Arg Asp Tyr Cys Asn Asp Leu Lys Ile Ser Asp Asn Asn Thr Glu Phe
    2990                2995                3000

CTT TTA AAT TTC AAC GAG TTT ATT GAT AGA AAA ACT CCA AAC AAC CCA      2068
Leu Leu Asn Phe Asn Glu Phe Ile Asp Arg Lys Thr Pro Asn Asn Pro
3005                3010                3015                3020

TCA TGT AAC GCG GAT TTG ATT AAT AGA GTC TTG CTT GAT GCA GGC TTT      2116
Ser Cys Asn Ala Asp Leu Ile Asn Arg Val Leu Leu Asp Ala Gly Phe
                3025                3030                3035

ACA AAT GAA CTT GTC CAA AAT TAC TGG AGT AAG CAG AAA AAT ATC AAG      2164
Thr Asn Glu Leu Val Gln Asn Tyr Trp Ser Lys Gln Lys Asn Ile Lys
            3040                3045                3050

GGA GTG AAA GCA CGA TTT GTT GTG ACT GAT GGT GGG ATT ACC AGA GTT      2212
Gly Val Lys Ala Arg Phe Val Val Thr Asp Gly Gly Ile Thr Arg Val
        3055                3060                3065

TAT CCC AAA GAG GCT GGA GAA AAT TGG CAA GAA AAC CCA GAG ACA TAT      2260
Tyr Pro Lys Glu Ala Gly Glu Asn Trp Gln Glu Asn Pro Glu Thr Tyr
    3070                3075                3080

GAG GAC AGC TTC TAT AAA AGG AGC CTA GAT AAT GAT AAC TAT GTT TTC      2308
Glu Asp Ser Phe Tyr Lys Arg Ser Leu Asp Asn Asp Asn Tyr Val Phe
3085                3090                3095                3100

ACT GCT CCC TAC TTT AAC AAA AGT GGA CCT GGT GCC TAT GAA TCG GGC      2356
Thr Ala Pro Tyr Phe Asn Lys Ser Gly Pro Gly Ala Tyr Glu Ser Gly
                3105                3110                3115

ATT ATG GTA AGC AAA GCT GTA GAA ATA TAT ATT CAA GGG AAA CTT CTT      2404
Ile Met Val Ser Lys Ala Val Glu Ile Tyr Ile Gln Gly Lys Leu Leu
            3120                3125                3130
```

```
AAA CCT GCA GTT GTT GGA ATT AAA ATT GAT GTA AAT TCC TGG ATA GAG      2452
Lys Pro Ala Val Val Gly Ile Lys Ile Asp Val Asn Ser Trp Ile Glu
            3135                3140                3145

AAT TTC ACC AAA ACC TCA ATC AGA GAT CCG TGT GCT GGT CCA GTT TGT      2500
Asn Phe Thr Lys Thr Ser Ile Arg Asp Pro Cys Ala Gly Pro Val Cys
    3150                3155                3160

GAC TGC AAA AGA AAC AGT GAC GTA ATG GAT TGT GTG ATT CTG GAT GAT      2548
Asp Cys Lys Arg Asn Ser Asp Val Met Asp Cys Val Ile Leu Asp Asp
3165                3170                3175                3180

GGT GGG TTT CTT CTG ATG GCA AAT CAT GAT GAT TAT ACT AAT CAG ATT      2596
Gly Gly Phe Leu Leu Met Ala Asn His Asp Asp Tyr Thr Asn Gln Ile
                3185                3190                3195

GGA AGA TTT TTT GGA GAG ATT GAT CCC AGC TTG ATG AGA CAC CTG GTT      2644
Gly Arg Phe Phe Gly Glu Ile Asp Pro Ser Leu Met Arg His Leu Val
            3200                3205                3210

AAT ATA TCA GTT TAT GCT TTT AAC AAA TCT TAT GAT TAT CAG TCA GTA      2692
Asn Ile Ser Val Tyr Ala Phe Asn Lys Ser Tyr Asp Tyr Gln Ser Val
    3215                3220                3225

TGT GAG CCC GGT GCT GCA CCA AAA CAA GGA GCA GGA CAT CGC TCA GCA      2740
Cys Glu Pro Gly Ala Ala Pro Lys Gln Gly Ala Gly His Arg Ser Ala
3230                3235                3240

TAT GTG CCA TCA GTA GCA GAC ATA TTA CAA ATT GGC TGG TGG GCC ACT      2788
Tyr Val Pro Ser Val Ala Asp Ile Leu Gln Ile Gly Trp Trp Ala Thr
3245                3250                3255                3260

GCT GCT GCC TGG TCT ATT CTA CAG CAG TTT CTC TTG AGT TTG ACC TTT      2836
Ala Ala Ala Trp Ser Ile Leu Gln Gln Phe Leu Leu Ser Leu Thr Phe
                3265                3270                3275

CCA CGA CTC CTT GAG GCA GTT GAG ATG GAG GAT GAT GAC TTC ACG GCC      2884
Pro Arg Leu Leu Glu Ala Val Glu Met Glu Asp Asp Asp Phe Thr Ala
            3280                3285                3290

TCC CTG TCC AAG CAG AGC TGC ATT ACT GAA CAA ACC CAG TAT TTC TTC      2932
Ser Leu Ser Lys Gln Ser Cys Ile Thr Glu Gln Thr Gln Tyr Phe Phe
    3295                3300                3305

GAT AAC GAC AGT AAA TCA TTC AGT GGT GTA TTA GAC TGT GGA AAC TGT      2980
Asp Asn Asp Ser Lys Ser Phe Ser Gly Val Leu Asp Cys Gly Asn Cys
3310                3315                3320

TCC AGA ATC TTT CAT GGA GAA AAG CTT ATG AAC ACC AAC TTA ATA TTC      3028
Ser Arg Ile Phe His Gly Glu Lys Leu Met Asn Thr Asn Leu Ile Phe
3325                3330                3335                3340

ATA ATG GTT GAG AGC AAA GGG ACA TGT CCA TGT GAC ACA CGA CTG CTC      3076
Ile Met Val Glu Ser Lys Gly Thr Cys Pro Cys Asp Thr Arg Leu Leu
                3345                3350                3355

ATA CAA GCG GAG CAG ACT TCT GAC GGT CCA AAT CCT TGT GAC ATG GTT      3124
Ile Gln Ala Glu Gln Thr Ser Asp Gly Pro Asn Pro Cys Asp Met Val
            3360                3365                3370

AAG CAA CCT AGA TAC CGA AAA GGG CCT GAT GTC TGC TTT GAT AAC AAT      3172
Lys Gln Pro Arg Tyr Arg Lys Gly Pro Asp Val Cys Phe Asp Asn Asn
    3375                3380                3385

GTC TTG GAG GAT TAT ACT GAC TGT GGT GGT GTT TCT GGA TTA AAT CCC      3220
Val Leu Glu Asp Tyr Thr Asp Cys Gly Gly Val Ser Gly Leu Asn Pro
3390                3395                3400

TCC CTG TGG TAT ATC ATT GGA ATC CAG TTT CTA CTA CTT TGG CTG GTA      3268
Ser Leu Trp Tyr Ile Ile Gly Ile Gln Phe Leu Leu Leu Trp Leu Val
3405                3410                3415                3420

TCT GGC AGC ACA CAC CGG CTG TTA TGACCT                               3298
Ser Gly Ser Thr His Arg Leu Leu
                3425
```

-continued (2) INFORMATION FOR SEQ ID NO:4:

(i) SEQUENCE CHARACTERISTICS:
        (A) LENGTH: 1091 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ala Gly Cys Leu Leu Ala Leu Thr Leu Thr Leu Phe Gln Ser
 1               5                  10                  15

Leu Leu Ile Gly Pro Ser Ser Glu Glu Pro Phe Pro Ser Ala Val Thr
             20                  25                  30

Ile Lys Ser Trp Val Asp Lys Met Gln Glu Asp Leu Val Thr Leu Ala
         35                  40                  45

Lys Thr Ala Ser Gly Val Asn Gln Leu Val Asp Ile Tyr Glu Lys Tyr
     50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                 85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Val Leu Lys Asp Ala
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365
```

-continued

```
Ala Gln Glu Ile Phe Asn Lys Tyr Asn Lys Asp Lys Val Arg Val
    370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
                420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Ala Leu Leu His Pro Asn Leu Gln
            515                 520                 525

Pro Lys Asn Pro Lys Ser Gln Glu Pro Val Thr Leu Asp Phe Leu Asp
530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
            595                 600                 605

Phe Tyr Tyr Ile Lys Ala Lys Leu Glu Glu Thr Ile Thr Gln Ala Arg
            610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Ala Asp
            675                 680                 685

Leu Ile Asn Arg Val Leu Leu Asp Ala Gly Phe Thr Asn Glu Leu Val
        690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
            755                 760                 765

Asn Lys Ser Gly Pro Gly Ala Tyr Glu Ser Gly Ile Met Val Ser Lys
770                 775                 780
```

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
            805                 810                 815

Ser Ile Arg Asp Pro Cys Ala Gly Pro Val Cys Asp Cys Lys Arg Asn
                820                 825                 830

Ser Asp Val Met Asp Cys Val Ile Leu Asp Gly Gly Phe Leu Leu
        835                 840                 845

Met Ala Asn His Asp Asp Tyr Thr Asn Gln Ile Gly Arg Phe Phe Gly
850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Val
                900                 905                 910

Ala Asp Ile Leu Gln Ile Gly Trp Trp Ala Thr Ala Ala Ala Trp Ser
            915                 920                 925

Ile Leu Gln Gln Phe Leu Leu Ser Leu Thr Phe Pro Arg Leu Leu Glu
930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Gly Glu Lys Leu Met Asn Thr Asn Leu Ile Phe Ile Met Val Glu Ser
            995                 1000                1005

Lys Gly Thr Cys Pro Cys Asp Thr Arg Leu Leu Ile Gln Ala Glu Gln
    1010                1015                1020

Thr Ser Asp Gly Pro Asn Pro Cys Asp Met Val Lys Gln Pro Arg Tyr
1025                1030                1035                1040

Arg Lys Gly Pro Asp Val Cys Phe Asp Asn Asn Val Leu Glu Asp Tyr
                1045                1050                1055

Thr Asp Cys Gly Gly Val Ser Gly Leu Asn Pro Ser Leu Trp Tyr Ile
            1060                1065                1070

Ile Gly Ile Gln Phe Leu Leu Leu Trp Leu Val Ser Gly Ser Thr His
            1075                1080                1085

Arg Leu Leu
    1090

(2) INFORMATION FOR SEQ ID NO:5:

(i) SEQUENCE CHARACTERISTICS:
        (A) LENGTH: 1476 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 8..1459

(xi) SEQUENCE DESCRIPTION: SEQ ID NO:5:

-continued

| | |
|---|---|
| CTCCCCC ATG TAT GAC GAC TCC TAC GTG CCC GGG TTT GAG GAC TCG GAG<br>        Met Tyr Asp Asp Ser Tyr Val Pro Gly Phe Glu Asp Ser Glu<br>                          1095                  1100                  1105 | 49 |
| GCG GGT TCA GCC GAC TCC TAC ACC AGC CGC CCA TCT CTG GAC TCA GAC<br>Ala Gly Ser Ala Asp Ser Tyr Thr Ser Arg Pro Ser Leu Asp Ser Asp<br>        1110                  1115                  1120 | 97 |
| GTC TCC CTG GAG GAG GAC CGG GAG AGT GCC CGG CGT GAA GTA GAG AGC<br>Val Ser Leu Glu Glu Asp Arg Glu Ser Ala Arg Arg Glu Val Glu Ser<br>        1125                  1130                  1135 | 145 |
| CAG GCT CAG CAG CAG CTC GAA AGG GCC AAG CAC AAA CCT GTG GCA TTT<br>Gln Ala Gln Gln Gln Leu Glu Arg Ala Lys His Lys Pro Val Ala Phe<br>        1140                  1145                  1150 | 193 |
| GCG GTG AGG ACC AAT GTC AGC TAC TGT GGC GTA CTG GAT GAG GAG TGC<br>Ala Val Arg Thr Asn Val Ser Tyr Cys Gly Val Leu Asp Glu Glu Cys<br>        1155                  1160                  1165 | 241 |
| CCA GTC CAG GGC TCT GGA GTC AAC TTT GAG GCC AAA GAT TTT CTG CAC<br>Pro Val Gln Gly Ser Gly Val Asn Phe Glu Ala Lys Asp Phe Leu His<br>1170                  1175                  1180                  1185 | 289 |
| ATT AAA GAG AAG TAC AGC AAT GAC TGG TGG ATC GGG CGG CTA GTG AAA<br>Ile Lys Glu Lys Tyr Ser Asn Asp Trp Trp Ile Gly Arg Leu Val Lys<br>        1190                  1195                  1200 | 337 |
| GAG GGC GGG GAC ATC GCC TTC ATC CCC AGC CCC CAG CGC CTG GAG AGC<br>Glu Gly Gly Asp Ile Ala Phe Ile Pro Ser Pro Gln Arg Leu Glu Ser<br>        1205                  1210                  1215 | 385 |
| ATC CGG CTC AAA CAG GAG CAG AAG GCC AGG AGA TCT GGG AAC CCT TCC<br>Ile Arg Leu Lys Gln Glu Gln Lys Ala Arg Arg Ser Gly Asn Pro Ser<br>        1220                  1225                  1230 | 433 |
| AGC CTG AGT GAC ATT GGC AAC CGA CGC TCC CCT CCG CCA TCT CTA GCC<br>Ser Leu Ser Asp Ile Gly Asn Arg Arg Ser Pro Pro Pro Ser Leu Ala<br>        1235                  1240                  1245 | 481 |
| AAG CAG AAG CAA AAG CAG GCG GAA CAT GTT CCC CCA TAT GAC GTG GTG<br>Lys Gln Lys Gln Lys Gln Ala Glu His Val Pro Pro Tyr Asp Val Val<br>1250                  1255                  1260                  1265 | 529 |
| CCC TCC ATG CGG CCT GTG GTG CTG GTG GGA CCC TCT CTG AAA GGT TAT<br>Pro Ser Met Arg Pro Val Val Leu Val Gly Pro Ser Leu Lys Gly Tyr<br>        1270                  1275                  1280 | 577 |
| GAG GTC ACA GAC ATG ATG CAG AAG GCT CTC TTC GAC TTC CTC AAA CAC<br>Glu Val Thr Asp Met Met Gln Lys Ala Leu Phe Asp Phe Leu Lys His<br>        1285                  1290                  1295 | 625 |
| AGA TTT GAT GGC AGG ATC TCC ATC ACC CGA GTC ACA GCC GAC CTC TCC<br>Arg Phe Asp Gly Arg Ile Ser Ile Thr Arg Val Thr Ala Asp Leu Ser<br>        1300                  1305                  1310 | 673 |
| CTG GCA AAG CGA TCT GTG CTC AAC AAT CCG GGC AAG AGG ACC ATC ATT<br>Leu Ala Lys Arg Ser Val Leu Asn Asn Pro Gly Lys Arg Thr Ile Ile<br>        1315                  1320                  1325 | 721 |
| GAG CGC TCC TCT GCC CGC TCC AGC ATT GCG GAA GTG CAG AGT GAG ATC<br>Glu Arg Ser Ser Ala Arg Ser Ser Ile Ala Glu Val Gln Ser Glu Ile<br>1330                  1335                  1340                  1345 | 769 |
| GAG CGC ATA TTT GAG CTG GCC AAA TCC CTG CAG CTA GTA GTG TTG GAC<br>Glu Arg Ile Phe Glu Leu Ala Lys Ser Leu Gln Leu Val Val Leu Asp<br>        1350                  1355                  1360 | 817 |
| GCT GAC ACC ATC AAC CAC CCA GCA CAG CTG GCC AAG ACC TCG CTG GCC<br>Ala Asp Thr Ile Asn His Pro Ala Gln Leu Ala Lys Thr Ser Leu Ala<br>        1365                  1370                  1375 | 865 |
| CCC ATC ATC GTC TTT GTC AAA GTG TCC TCA CCA AAG GTA CTC CAG CGT<br>Pro Ile Ile Val Phe Val Lys Val Ser Ser Pro Lys Val Leu Gln Arg<br>        1380                  1385                  1390 | 913 |
| CTC ATT CGC TCC CGG GGG AAG TCA CAG ATG AAG CAC CTG ACC GTA CAG<br>Leu Ile Arg Ser Arg Gly Lys Ser Gln Met Lys His Leu Thr Val Gln<br>        1395                  1400                  1405 | 961 |

```
ATG ATG GCA TAT GAT AAG CTG GTT CAG TGC CCA CCG GAG TCA TTT GAT         1009
Met Met Ala Tyr Asp Lys Leu Val Gln Cys Pro Pro Glu Ser Phe Asp
1410            1415                1420                1425

GTG ATT CTG GAT GAG AAC CAG CTG GAG GAT GCC TGT GAG CAC CTG GCT         1057
Val Ile Leu Asp Glu Asn Gln Leu Glu Asp Ala Cys Glu His Leu Ala
                1430                1435                1440

GAG TAC CTG GAG GTT TAC TGG CGG GCC ACG CAC CAC CCA GCC CCT GGC         1105
Glu Tyr Leu Glu Val Tyr Trp Arg Ala Thr His His Pro Ala Pro Gly
            1445                1450                1455

CCC GGA CTT CTG GGT CCT CCC AGT GCC ATC CCC GGA CTT CAG AAC CAG         1153
Pro Gly Leu Leu Gly Pro Pro Ser Ala Ile Pro Gly Leu Gln Asn Gln
        1460                1465                1470

CAG CTG CTG GGG GAG CGT GGC GAG GAG CAC TCC CCC CTT GAG CGG GAC         1201
Gln Leu Leu Gly Glu Arg Gly Glu Glu His Ser Pro Leu Glu Arg Asp
    1475                1480                1485

AGC TTG ATG CCC TCT GAT GAG GCC AGC GAG AGC TCC CGC CAA GCC TGG         1249
Ser Leu Met Pro Ser Asp Glu Ala Ser Glu Ser Ser Arg Gln Ala Trp
1490                1495                1500                1505

ACA GGA TCT TCA CAG CGT AGC TCC CGC CAC CTG GAG GAG GAC TAT GCA         1297
Thr Gly Ser Ser Gln Arg Ser Ser Arg His Leu Glu Glu Asp Tyr Ala
                1510                1515                1520

GAT GCC TAC CAG GAC CTG TAC CAG CCT CAC CGC CAA CAC ACC TCG GGG         1345
Asp Ala Tyr Gln Asp Leu Tyr Gln Pro His Arg Gln His Thr Ser Gly
            1525                1530                1535

CTG CCT AGT GCT AAC GGG CAT GAC CCC CAA GAC CGG CTT CTA GCC CAG         1393
Leu Pro Ser Ala Asn Gly His Asp Pro Gln Asp Arg Leu Leu Ala Gln
        1540                1545                1550

GAC TCA GAA CAC AAC CAC AGT GAC CGG AAC TGG CAG CGC AAC CGG CCT         1441
Asp Ser Glu His Asn His Ser Asp Arg Asn Trp Gln Arg Asn Arg Pro
    1555                1560                1565

TGG CCC AAG GAT AGC TAC TGACAGCCTC CTGCTGC                              1476
Trp Pro Lys Asp Ser Tyr
1570                1575

(2) INFORMATION FOR SEQ ID NO:6:

(i) SEQUENCE CHARACTERISTICS:
        (A) LENGTH: 484 amino acids
        (B) TYPE: amino acid
        (D) TOPOLOGY: linear (ii) MOLECULE TYPE: protein (xi) SEQUENCE DESCRIPTION: SEQ ID NO:6:

Met Tyr Asp Asp Ser Tyr Val Pro Gly Phe Glu Asp Ser Glu Ala Gly
1               5                   10                  15

Ser Ala Asp Ser Tyr Thr Ser Arg Pro Ser Leu Asp Ser Asp Val Ser
                20                  25                  30

Leu Glu Glu Asp Arg Glu Ser Ala Arg Arg Glu Val Glu Ser Gln Ala
            35                  40                  45

Gln Gln Gln Leu Glu Arg Ala Lys His Lys Pro Val Ala Phe Ala Val
        50                  55                  60

Arg Thr Asn Val Ser Tyr Cys Gly Val Leu Asp Glu Glu Cys Pro Val
65                  70                  75                  80

Gln Gly Ser Gly Val Asn Phe Glu Ala Lys Asp Phe Leu His Ile Lys
                85                  90                  95

Glu Lys Tyr Ser Asn Asp Trp Trp Ile Gly Arg Leu Val Lys Glu Gly
            100                 105                 110
```

-continued

```
Gly Asp Ile Ala Phe Ile Pro Ser Pro Gln Arg Leu Glu Ser Ile Arg
        115                 120                 125

Leu Lys Gln Glu Gln Lys Ala Arg Arg Ser Gly Asn Pro Ser Ser Leu
130                 135                 140

Ser Asp Ile Gly Asn Arg Arg Ser Pro Pro Pro Ser Leu Ala Lys Gln
145                 150                 155                 160

Lys Gln Lys Gln Ala Glu His Val Pro Pro Tyr Asp Val Val Pro Ser
                165                 170                 175

Met Arg Pro Val Val Leu Val Gly Pro Ser Leu Lys Gly Tyr Glu Val
                180                 185                 190

Thr Asp Met Met Gln Lys Ala Leu Phe Asp Phe Leu Lys His Arg Phe
                195                 200                 205

Asp Gly Arg Ile Ser Ile Thr Arg Val Thr Ala Asp Leu Ser Leu Ala
                210                 215                 220

Lys Arg Ser Val Leu Asn Asn Pro Gly Lys Arg Thr Ile Ile Glu Arg
225                 230                 235                 240

Ser Ser Ala Arg Ser Ser Ile Ala Glu Val Gln Ser Glu Ile Glu Arg
                245                 250                 255

Ile Phe Glu Leu Ala Lys Ser Leu Gln Leu Val Val Leu Asp Ala Asp
                260                 265                 270

Thr Ile Asn His Pro Ala Gln Leu Ala Lys Thr Ser Leu Ala Pro Ile
            275                 280                 285

Ile Val Phe Val Lys Val Ser Ser Pro Lys Val Leu Gln Arg Leu Ile
            290                 295                 300

Arg Ser Arg Gly Lys Ser Gln Met Lys His Leu Thr Val Gln Met Met
305                 310                 315                 320

Ala Tyr Asp Lys Leu Val Gln Cys Pro Pro Glu Ser Phe Asp Val Ile
                325                 330                 335

Leu Asp Glu Asn Gln Leu Glu Asp Ala Cys Glu His Leu Ala Glu Tyr
                340                 345                 350

Leu Glu Val Tyr Trp Arg Ala Thr His His Pro Ala Pro Gly Pro Gly
                355                 360                 365

Leu Leu Gly Pro Pro Ser Ala Ile Pro Gly Leu Gln Asn Gln Gln Leu
            370                 375                 380

Leu Gly Glu Arg Gly Glu Glu His Ser Pro Leu Glu Arg Asp Ser Leu
385                 390                 395                 400

Met Pro Ser Asp Glu Ala Ser Glu Ser Ser Arg Gln Ala Trp Thr Gly
                405                 410                 415

Ser Ser Gln Arg Ser Ser Arg His Leu Glu Glu Asp Tyr Ala Asp Ala
                420                 425                 430

Tyr Gln Asp Leu Tyr Gln Pro His Arg Gln His Thr Ser Gly Leu Pro
            435                 440                 445

Ser Ala Asn Gly His His Asp Pro Gln Asp Arg Leu Leu Ala Gln Asp Ser
        450                 455                 460

Glu His Asn His Ser Asp Arg Asn Trp Gln Arg Asn Arg Pro Trp Pro
465                 470                 475                 480

Lys Asp Ser Tyr
```

NUCLEIC ACID ENCODING HUMAN NEURONAL CALCIUM CHANNEL SUBUNITS

RELATED APPLICATION

This application is a Divisional of U.S. application Ser. No. 08/713,118 filed Sep. 16, 1996 now U.S. Pat. No. 6,040,436, the entire teachings of which are incorporated herein by reference.

BACKGROUND OF THE INVENTION

Calcium channels are multi-subunit protein complexes that span the plasma membrane and are involved in the movement of calcium ions into the cell. Voltage-dependent calcium channels, the most common type of calcium channels, are classified as L-, T-, N-, or P-type channels, based on conductance levels, sensitivity to agonists and antagonists, and holding potential (K. Dunlap et al., *Trends Neurosci.* 18:89–98 (1995)). Calcium channels contain two large subunits, α1 and α2, having molecular weights between about 130 and about 200 kDa, and one to three smaller subunits, such as β, and/or γ subunits, each having a molecular weight that is usually less than about 60 kDa. At least one of the large subunits is glycosylated, and a smaller subunit may be glycosylated as well. Subunit α1 is approximately 200 to about 230 kDa, based on sodium dodecylsulfate polyacrylamide gel electrophoresis (SDS-PAGE). This subunit forms the pore through which calcium enters cells. Subunit α2 is approximately 160 to 190 kDa under non-reducing conditions on SDS-PAGE. The β subunit is about 52 to 65 kDa (SDS-PAGE); it is insensitive to reducing conditions. The γ subunit, which is not observed in nervous tissue or in other certain preparations, is a glycoprotein of approximately 30 to 33 kDa (SDS-PAGE).

Investigation of particular calcium channel subtypes is rendered difficult by the presence of a mixture of different tissue-specific types of calcium channels in cells. Study of particular subtypes is essential, however, because of the importance of intracellular calcium levels in contributing to vital cellular processes including neurotransmitter release, muscle contraction, pacemaker activity, and secretion of hormones and other substances. A need remains for identifying and studying individual calcium channel subtypes.

SUMMARY OF THE INVENTION

The current invention pertains to the isolation and sequencing of nucleic acids encoding three subunits of human N-type calcium channel: an α1B subunit, an α2δ subunit, and a β3 subunit. Previously unknown alterations are present in the sequence of nucleotides encoding each of the subunits. The nucleic acid encoding the α1B subunit has a change from G to A at position 194; a change from T to G at position 2559; a change from G to A at position 6470; and a deletion of nucleotides 4814–4819. The nucleic acid encoding the α2δ subunit has a change from A to C at position 329; a change from G to C at position 1191; a change from G to C at position 1219; a change from T to C at position 1596; a change from T to C at position 1980; a change from A to G at position 2090; and a change from A to G at position 3261. The nucleic acid encoding the β3 subunit has a change from C to G at position 46; a TCC insertion at position 119; a change from A to T at position 203; a change from C to T at position 300; a change from C to G at position 303; a change from A to G at position 420; a change from C to T at position 438; a change from T to C at position 477; a change from T to G at position 486; a change from G to A at position 534; a change from A to C at position 552; a change from G to T at position 561; an ATG insertion at position 978; a change from T to A at position 1064; a change from CG to GC at positions 1283–1284; or a change from C to T at position 1308. Certain of these changes result in amino acid alterations in the encoded proteins, while others are synonymous changes. Vectors containing the nucleic acids encoding the subunits described above have been prepared, as have host cells containing the nucleic acids. Methods of isolating nucleic acids encoding related calcium channel subunits, by employing hybridization of the nucleic acids of the invention to nucleic acid libraries, are now available by virtue of the discoveries described herein. Also available are the subunit proteins encoded by the nucleic acids, and also fusion proteins comprising the subunit proteins. Antibodies to the subunit proteins can also be generated. Assays to identify agents that modulate calcium channel activity are described, in which test cells are exposed to the agent to be tested and a calcium channel-selective ion; depolarizing the cell membrane of the test cell; detecting current flowing into the cell; and comparing the current to that of a control cell, wherein a difference in the current detected in the test cell, as compared with the current of the control cell, indicates that the agent modulates calcium channel activity. In addition, methods of diagnosing diseases associated with particular calcium channels, such as Lambert-Eaton syndrome, are described, using assays to detect the presence of calcium channel-specific antibodies in a sample from the individual suspected of having the disease.

The changes that are present in the subunits described herein may produce functional differences in the calcium channel formed by the three subunits, which will have an effect on the interaction between the calcium channels and agonists or antagonists of the channels. Furthermore, calcium channel subunits described herein are an advantageous combination, because the β3 subunit is normally found associated with an α1B subunit in vivo, thus, this combination closely resembles the calcium channel in vivo.

BRIEF DESCRIPTION OF THE DRAWING

The FIGURE is a graphic representation of average counts per minute (CPM) for omega-conotoxin GVIA-sensitive potassium-stimulated calcium uptake in cells transfected with the three human calcium channel subunits.

DETAILED DESCRIPTION OF THE INVENTION

The current invention pertains to the isolation and identification of DNA encoding subunits of a particular calcium channel. As described in the Examples below, cDNA encoding an α1B subunit, an α2δ subunit, and a β3 subunit of the human N-type calcium channel has been isolated. The cDNA clones have been inserted into expression vectors, and are stably expressed in transformed cell lines. The resulting transformed cells express each of the three mRNA encoding the individual subunits of the N-type channel. The transformed cells show omega-conotoxin GVIA binding activity, and omega-conotoxin GVIA toxin sensitive potassium-stimulated calcium uptake, indicating that the proteins expressed by the clones are capable of forming a functioning calcium channel.

As a result of this discovery, nucleic acids encoding the three subunits, as well as vectors containing the nucleic acids encoding one or more of the subunits, host cells containing the nucleic acids encoding one or more of the subunits, and methods of isolating nucleic acids encoding related calcium channel subunits are now available. The subunit proteins, fusion proteins comprising the subunit proteins, and antibodies to the subunit proteins, as well as assays to identify agents that modulate calcium channel activity, are also described. Agents that modulate calcium channel activity can be used to treat certain central nervous system disorders by altering calcium channel activity. In addition, methods of diagnosing diseases associated with particular calcium channels, such as Lambert-Eaton syndrome, are described.

A "nucleic acid encoding a calcium channel subunit", as used herein, is a sequence of nucleotides which encodes either an α1B subunit, an α2δ subunit, or a β3 subunit of the N-type calcium channel. Nucleic acid encoding a calcium channel subunit can be either cDNA, DNA or mRNA. The nucleic acid encoding a calcium channel subunit is "isolated," indicating that it has been purified according to standard techniques known in the art (for example, such as by techniques described by Sambrook et al. (eds), in Molecular Cloning: A Laboratory Manual, (2nd ed.), Cold Spring Harbor Laboratory Press (1989)).

In one embodiment, nucleic acid encoding a calcium channel α1B subunit has the sequence of SEQ ID NO. 1. In another embodiment, nucleic acid encoding a calcium channel α1B subunit is a nucleic acid encoding a functional equivalent of the subunit encoded by sequence of SEQ ID NO. 1. A "functional equivalent" has the same function as the calcium channel subunit, but is encoded by a nucleic acid that may have minor variations in the sequence of nucleotides, in comparison to the nucleic acid encoding the subunit. A nucleic acid encoding a functional equivalent is referred to herein as an "equivalent" nucleic acid. Minor variations in equivalent nucleic acids include variations that result in no alteration of the encoded amino acid sequence (synonymous changes); variations that result in conservative amino acid substitutions in the encoded amino acid sequence; and/or minor deletions or insertions of nucleotides that do not alter the activity of the peptide. Such changes are readily known to the skilled artisan. For example, representative conservative amino acid changes include: alanine to glycine or serine; arginine to lysine; asparagine to glutamine or histidine; cysteine to serine; glutamine to asparagine; glutamate to aspartate; glycine to alanine or proline; histidine to asparagine or glutamine; isoleucine to leucine or valine; leucine to isoleucine or valine; lysine to arginine or glutamine; methionine to leucine tyrosine, or isoleucine; phenylalanine to methionine, leucine to tyrosine; serine to threonine; threonine to serine; tryptophan to tyrosine; tyrosine to tryptophan or phenylalanine; valine to isoleucine or leucine.

A functional equivalent of a subunit has an activity that is equivalent to the subunit. "Activity" refers to the ability of the peptide to form a functional calcium channel with other necessary subunits. A functional calcium channel is a calcium channel that is able to provide for and regulate entry of calcium channel-selective ions, including calcium, in response to appropriate stimuli, and/or is able to bind ligands having affinity for the calcium channel. The activity of a calcium channel may be assessed in vitro by standard methods, such as electrophysiological or other methods described below.

Nucleic acids encoding a functional equivalent of a calcium channel α1B subunit, include at least one of the following alterations, in comparison to the nucleic acid sequence in the GenBank sequence data base, Accession number M94172 (see Williams, M. E. et al., Science 257:389–395 (1992)): a change from G to A change at position 194; a change from T to G at position 2559; a change from G to A at position 6470; or a deletion of nucleotides 4814–4819. The nucleic acid having the sequence of SEQ ID NO. 1, as well as nucleic acids encoding a functional equivalent of the subunit encoded by the sequence of SEQ ID NO. 1, are collectively referred to herein as a nucleic acid encoding a calcium channel α1B subunit.

A nucleic acid encoding a calcium channel α2δ subunit has the sequence of SEQ ID NO. 3, or a sequence of nucleotides encoding a functional equivalent of the subunit encoded by the nucleic acid shown in SEQ ID NO. 3. A nucleic acid encoding a functional equivalent of the subunit encoded by the sequence of SEQ ID NO. 3 includes at least one of the following alterations, in comparison to the GenBank sequence data base, Accession number M94172 (Williams, M. E. et al., Neuron 8:71–84 (1992)): a change from A to C at position 329; a change from G to C at position 1191; a change from G to C at position 1219; a change from T to C at position 1596; a change from T to C at position 1980; a change from A to G at position 2090; or a change from A to G at position 3261.

A nucleic acid encoding a calcium channel β3 subunit has the sequence of SEQ ID NO. 5, or the sequence of nucleotides encoding a functional equivalent of the subunit encoded by the nucleic acid shown in SEQ ID NO. 5. A sequence of nucleotides encoding a functional equivalent of the subunit encoded by the nucleic acid shown in SEQ ID NO. 5 includes at least one of the following alterations, in comparison to the GenBank sequence data base, Accession number L27584 (see Collin, T. et al., Eur. J. Biochem. 220(1):257–262 (1994)): a change from C to G at position 46; a TCC insertion at position 119; a change from A to T at position 203; a change from C to T at position 300; a change from C to G at position 303; a change from A to G at position 420; a change from C to T at position 438; a change from T to C at position 477; a change from T to G at position 486; a change from G to A at position 534; a change from A to C at position 552; a change from G to T at position 561; an ATG insertion at position 978; a change from T to A at position 1064; a change from CG to GC at positions 1283–1284; or a change from C to T at position 1308.

The nucleic acids encoding calcium channel subunits of the invention can be used to isolate other nucleic acids encoding related subunits. For example, all or a portion of one of the nucleic acids encoding a calcium channel subunit can be used as a probe to isolate nucleic acids from a nucleic acid library by hybridization techniques. A "portion" of the nucleic acid indicates a part of the nucleic acid that contains one of the specific alterations described above. Stringency conditions should be tailored to eliminate hybridization of the probes to extraneous nucleic acid sequences (see Sambrook et al. (eds), Molecular Cloning: A Laboratory Manual, (2nd cd.), Cold Spring Harbor Laboratory Press (1989), particularly chapter 11.45). In a preferred embodiment, stringency conditions are selected such that the nucleic acid encoding, a calcium channel subunit, or a portion of the nucleic acid, selectively hybridizes to a second nucleic acid (the target nucleic acid). "Selective hybridization" indicates that the hybridization is of sufficient specificity to allow the target nucleic acid to be identified or isolated from other nucleic acids. Generally, medium stringency conditions will allow selective hybridization. Nucleic acids that encode a calcium channel subunit, and are capable of selectively hybridizing, under medium or high stringency conditions, to all or a portion of a nucleic acid encoding a calcium channel subunit of the invention, or to all or a portion of a nucleic acid encoding a functional equivalent of a calcium channel subunit of the invention, are also encompassed by the invention.

Nucleic acids encoding a calcium channel α1B subunit, a calcium channel α2δ subunit, or a calcium channel β3 subunit, as described above, can be inserted into a vector to facilitate expression. The vector is capable of expressing nucleic acids that are in operative linkage with endogenous or exogenous regulatory sequences; it may be a plasmid, a phage, a virus, or other vector. The vector can contain other elements, such as transcriptional promoter elements, enhancer elements, splicing signals, termination and polyadenylation signals, viral replicons, and/or bacterial plasmid sequences. Upon introduction of the vector into a host cell, the nucleic acid inserted into the vector is expressed. The vector can contain more than one nucleic acid encoding a calcium channel subunit of the invention. For example, a vector can contain nucleic acids encoding a calcium channel α1B subunit, as well as nucleic acids encoding a calcium channel α2δ subunit. If only one subunit is used, it is understood that other known sequences are present to encode a functional protein.

A vector containing the nucleic acids encoding a calcium channel subunit of the invention, as described above, can be transformed or transfected into an appropriate host cell for expression. Alternatively, a nucleic acid encoding a calcium channel subunit of the invention can be inserted directly into the host cell. The nucleic acids can be introduced into the cell in a manner such that they are integrated into the host cell genome; alternatively, they can be maintained episomally.

Representative host cells include *Escherichia coli*, HEK 293 cells, Chinese hamster ovary (CHO) cells, African green monkey cells, mouse L cells, amphibian oocytes, and CHODUX cells (Mitchell, P. J. et al., *Mol. Cell Biol.* 6(6)1926–35 (1986)). In a preferred embodiment, the host cell does not naturally contain nucleic acids encoding, or produce calcium channels comprising, α1B, α2δ, or β3 subunits, in order to facilitate distinguishing the nucleic acids and encoded subunits of the invention from other, native nucleic acids and subunits. In a more preferred embodiment, the host cell does not express or produce endogenous calcium channel subunits of the type, or in an amount, that substantially interferes with detection of the nucleic acids and encoded subunits of the invention.

A single α1 subunit is sufficient to form a calcium channel; therefore, at least the nucleic acid encoding the α1B subunit is introduced into the host cell. In a preferred embodiment, nucleic acids encoding each of the three subunits are introduced into the host cell such that the host cell expresses the subunits and includes one or more of them in membrane-spanning calcium channels. In a preferred embodiment, the host cell expresses functional calcium channels that are capable of controlling movement of calcium channel-selective ions and/or binding compounds. In a more preferred embodiment, the calcium channels are composed substantially or entirely of the three subunits encoded by the nucleic acids of the invention, in order to generate a calcium channel that is closer to the normal physiologic state of the channel in the mammalian central nervous system. A host cell which has been transformed or transfected as described above is also referred to herein as a transformed cell.

Host cells transformed or transfected with nucleic acids encoding one or more of the calcium channel subunits of the invention can be used for screening for compounds that modulate calcium channel activity. Because the host cells have a homogeneous population of calcium channels, they provide a means to identify agents that specifically modulate activity of the particular calcium channels. An agent that modulates (e.g., enhances or upregulates, or inhibits or downregulates) calcium channel activity is an agent that affects the ability of the calcium channel to pass calcium channel-selective ions, or affects other detectable calcium channel characteristics, such as current kinetics. The agent may affect the calcium channel directly or indirectly.

For example, transformed cells can be used in assays that identify agents that are agonists or antagonists of calcium channel activity. To identify agents that modulate calcium channel activity, a transformed cell (or a culture of transformed cells), used as a "test" cell, is maintained in a solution containing an agent to be tested for its ability to modulate calcium channel activity (the test agent) and a calcium channel selective ion. A "calcium channel selective ion" refers to an ion that is capable of flowing through, or being blocked from flowing through, a calcium channel which spans a cellular membrane under conditions which would permit or block the flow of calcium ions. $Ba^{2+}$ is an example of a calcium channel selective ion. The cell membrane of the test cell is then depolarized, and current flowing into the test cell is detected. If the current that is detected is different from the current produced by depolarizing the same cell or a control cell in the presence of the same calcium channel selective ion, but in the absence of the compound, then the agent modulates calcium channel activity. In a preferred embodiment, the test cell is maintained at a holding potential which substantially inactivates calcium channels prior to the depolarization step. If the current is higher in the presence of the agent than in the absence of the agent, then the agent is an agent that enhances calcium channel activity (a calcium channel agonist). If the current is lower in the presence of the agent than in the absence of the agent, then the agent is an agent that inhibits calcium channel activity (a calcium channel antagonist).

One "control" cell which can be used as described above, is a cell that is maintained in substantially the same manner as the test cell, with the exception that the control cell is not exposed to the agent to be tested. An alternative "control" cell is a cell which is identical to the test cell, except that it does not express functional calcium channels.

Agents identified by these methods can be used to modulate activity of calcium channels in vivo. The in vitro assays described above should accurately predict relative efficacy of an agent as an agonist or an antagonist of calcium channels, since the calcium channel subunits described herein are subtype- and tissue-specific. Specific disease targets include central nervous system disorders, including stroke, cerebral ischemia, epilepsy, chronic pain, head trauma, and other central nervous system diseases or conditions in which too much or too little neurotransmitter is released. The agent is administered by an appropriate route, such as orally, subcutaneously, transdermally, intravenously, intramuscularly, intraperitoneally, topically, rectally, vaginally, nasally, or via an implanted reservoir. The agent can be administered in dosage formulations containing conventional, non-toxic, physiologically-acceptable carriers, adjuvants, and/or vehicles. The formulation in which the agent is administered will depend at least in part on the route by which it is administered. The agent is administered in an effective amount, which is that amount necessary to alleviate, reduce, eliminate, or prevent the symptoms associated with the disease, disorder or condition to be treated. More than one agent can be administered; if more than agent is used, the effective amount is that amount of the combination of agents that is necessary to alleviate, reduce, eliminate or prevent the symptoms associated with disease, disorder or condition. The effective amount will be determined on an individual basis, and will be based in part, on consideration of the particular agent, the individual's size and gender, the severity of the symptoms to be treated, the result sought, and the disease, disorder or condition to be treated. The effective amount can be administered in a series of doses separated by appropriate intervals, such as hours, days, or weeks. Alternatively, the effective amount can be administered as a sustained release dose, such as by a controlled-release dosage formulation.

Purified proteins encoded by a nucleic acid encoding a calcium channel α1B subunit, a calcium channel α2δ subunit, or a calcium channel β3 subunit, as described above, are also described. The proteins (also referred to herein as calcium channel subunits of the invention) can be isolated from a host cell transfected or transformed with the nucleic acid encoding the subunit. Representative proteins include a calcium channel α1B subunit having the amino acid sequence of SEQ ID NO. 2; a calcium channel α2δ subunit having the amino acid sequence of SEQ ID NO. 4; or a calcium channel β3 subunit having the amino acid sequence of SEQ ID NO. 6.

Fusion proteins comprising the calcium channel α1B subunit, a calcium channel α2δ subunit, or a calcium channel β3 subunit can also be generated using standard techniques. For example, a fusion nucleic acid can be generated by splicing, or attaching the nucleic acid encoding the calcium channel subunit to a nucleic acid encoding another protein or peptide (the fusion partner or protein), or by inserting the nucleic acid encoding the calcium channel subunit and the fusion protein into a common vector; the fusion nucleic acid can then be transformed, transfected, or inserted into a host cell for transcription and translation.

Antibodies (or immunoglobulins) to the calcium channel subunits of the invention can be generated. The term "antibody", as used herein, encompasses both polyclonal and monoclonal antibodies, as well as mixtures of more than one antibody reactive with a calcium channel subunit of the invention (e.g., a cocktail of different types of monoclonal antibodies reactive with the mutant protein or protein fragment). The term antibody is further intended to encompass whole antibodies and/or biologically functional fragments thereof, chimeric antibodies comprising portions from more than one species, humanized antibodies, human-like antibodies, and bifunctional antibodies. Biologically functional antibody fragments which can be used are those fragments sufficient for binding of the antibody fragment to the calcium channel subunit of interest. Once the antibodies are raised, they are assessed for the ability to bind to the calcium channel subunit of interest. Conventional methods can be used to perform this assessment. Antibodies can also be raised to calcium channels formed by the combination of the calcium channel α1B subunit, the calcium channel α2δ subunit, and the calcium channel β3 subunit described herein.

The chimeric antibodies can comprise portions derived from two different species (e.g., a constant region from one species and variable or binding regions from another species). The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins.

Monoclonal antibodies (mAb) reactive with a calcium channel subunit of the invention, or a calcium channel formed by the subunits, can be produced using somatic cell hybridization techniques (Kohler and Milstein, Nature 256: 495–497 (1975)) or other techniques. In a typical hybridization procedure, purified calcium channel subunit, or calcium channels, can be used as the immunogen. An animal is immunized with the immunogen to obtain antibody-producing spleen cells. The species of animal immunized will vary depending on the specificity of mAb desired. The antibody producing cell is fused with an immortalizing cell (e.g., a myeloma cell) to create a hybridoma capable of secreting antibodies. The unfused residual antibody-producing cells and immortalizing cells are eliminated. Hybridomas producing desired antibodies are selected using conventional techniques and the selected hybridomas are cloned and cultured.

Polyclonal antibodies can be prepared by immunizing an animal in a similar fashion as described above for the production of monoclonal antibodies. The animal is maintained under conditions whereby antibodies reactive with the calcium channel subunit of interest, or the calcium channel, are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG, IgM).

Antibodies that are specific for the calcium channel subunits of the invention, or for the calcium channel formed by the three subunits of the invention, can be used for immunohistochemistry to monitor distribution and expression density of the various subunits, or of the calcium channels themselves, in different tissues, including in normal and in diseased tissue. The antibodies can also be used as a therapeutic agent, in order to modulate calcium channel activity, as described in detail above.

Antibodies that are specific for the calcium channel subunits of the invention, or for the calcium channel formed by the three subunits of the invention, can also be used to facilitate diagnosis of Lambert-Eaton Syndrome (LES). LES autoimmune disease is characterized by insufficient release of acetylcholine from motor nerve terminals which normally are responsive to nerve impulses. IgG from LES patients block individual voltage-dependent calcium channels and thus inhibit calcium channel activity (Kim and Neher, Science 239:405–8 (1988)). To diagnose LES, a test sample of blood or other bodily fluid is obtained from an individual suspected of having or carrying the disease. The test sample is contacted with a calcium channel subunit of the invention, or a calcium channel formed by the three subunits of the invention, under conditions which would allow any antibody which is specific for the calcium channel subunit or the calcium channel, and which may be present in the test sample, to bind. Binding of antibody to the calcium channel subunit of the invention, or the calcium channel formed by the subunits of the invention, if such binding exists, is then detected. The presence of binding indicates that the individual has antibodies to the calcium channel, and thus, is afflicted with LES.

The invention is further illustrated by the following Examples.

EXAMPLE 1

Isolation and Expression of Clones for Human α1B Subunit of N-Type Channel

Sequences referred to herein are described in comparison to the sequence encoding an α1B subchannel, described in the GenBank sequence data base, Accession number M94172 (see Williams, M. E. et al., *Science* 257:389–395 (1992)).

A. Isolation of Primary Clones

Three primary clones, each containing a portion of the $\alpha_{1B}$ subunit, were obtained by hybridization under low stringency conditions with human cerebellum library at 50° C. in 6× sodium chloride, sodium citrate (SCC) overnight. Hybridized nucleic acids were washed using standard techniques (see Sambrook et al. (eds), Molecular Cloning: A Laboratory Manual, (2nd ed.), Cold Spring Harbor Laboratory Press (1989)).

First, clone pN, which spans sequences 54–1405, was cloned into the SmaIsite of pSK-(Bluescript). The SacI site of the polylinker is at the 5' end. The SmaI site was destroyed. pN has a single nucleotide change (G to A at position 194), which alters the amino acid at the corresponding position in the protein from gly to ser.

The second clone, pM, spans sequences 978–4562. EcoRI/blunt fragment was inserted into EcoRI/SmaI sites of pSK-. The KpnI site of the polylinker was at the 5' end. The SmaI site was destroyed. pM has a single nucleotide change (T to G at position 2559), which results in an alteration of the amino acid at the corresponding position from leu to arg.

Clone pC, which spans sequences 4105–7322, was also isolated. An EcoRI/XbaI fragment was cloned into EcoRI/XbaI restricted pNK-CMV vector. The SacI site of the polylinker is at the 5' end. Clone pC has two changes: a single nucleotide change at position 6470 (G to A), resulting in an alteration of the corresponding amino acid from gly to ser; and a six base pair deletion at nucleic acid positions 4814–4819, resulting in a deletion of the two corresponding amino acids (glu and thr).

B. Generation of pSK-Hα1

In order to generate a clone containing the entire α1B cDNA, combination vectors were made. First, pMC was created. To allow cleavage by MamI, both pM and pC were transformed into SCS 110 cells (Stratagene; dam-, dcm-), and the unmethylated DNA was isolated. pC was digested with XbaI and MamI, and the 2930 bp fragment was isolated. pM was also digested with MamI and XbaI, and the 6.4 kb vector+insert band was isolated. These two fragments were ligated together to create pMC. The fusion point is the MamI site at position 4395.

pNMC, a fusion of pN and pMC, was then generated. pN was restricted with KpnI and XbaI, and the 1.4 kb insert was isolated. pMC was restricted with XbaI and partially restricted with KpnI. The 6012 XbaI/KpnI fragment was isolated. These two fragments were ligated together, and the ligation reaction was then cut with XbaI. The resulting fragments were then ligated to a pSK- vector restricted with XbaI. The resulting plasmid contains the entire coding sequence of α1, with 91 bp 5' UT, and 157 bp 3' UT (pos 54–7322) the fusion point is the KpnI site at position 1310. The KpnI site of the pSK- polylinker is at the 5' end. This pNMC vector is referred to as pSK-Hα1.

C. Expression Clones

Two expression clones were generated. The first, pNK-Hα1, was constructed by isolating the XbaI insert of pSK-Hα1; this XbaI insert was inserted into the XbaI site of pNK-CMV. The polylinker SacI site is at the 5' end.

A second expression clone, pNK-Hα1-Koz, was also generated. A 5' primer containing an optimized Kozak sequence (CCACC<u>ATGG</u>) (SEQ ID NO. 7), an EcoRI site, and surrounding bases was synthesized. A 3' primer spanning the BglII site at position 1463 was also synthesized. These primers were used to PCR the α1 5' end from pNK-Hα1. This product was cut with EcoRI and BglII, and cloned into a likewise restricted pNK-Hα1 plasmid. The resulting truncated plasmid contains the Kozak sequence and has been shown to express at least as well as the parent plasmid in transient transfection studies.

The Hα1 gene thus includes several changes from the previously known sequence presented in the GenBank sequence data base, Accession number M94172. A single nucleotide change (G to A at position 194), alters the amino acid at the corresponding position in the protein from gly to ser; a single nucleotide change (T to G at position 2559), results in an alteration of the amino acid at the corresponding position from leu to arg. Also, a single nucleotide change at position 6470 (G to A), results in an alteration of the corresponding amino acid from gly to ser; and a six base pair deletion at nucleic acid positions 4814–4819, results in a deletion of the two corresponding amino acids (glu and thr). These alterations are summarized in Table I.

TABLE I

α1B Alterations

| Position | Nucleotide Change | Amino Acid Change |
|---|---|---|
| 194 | G to A | Gly to Ser |
| 2559 | T to G | Leu to Arg |
| 6470 | G to A | Gly to Ser |
| 4814–4819 | Deletion 6 bp | Deletion Glu and Thr |

EXAMPLE 2

Isolation and Expression of Clones for Human α2δ Subunit of N-Type Channel

Sequences referred to herein are described in comparison to the sequence encoding an α2δ subchannel, described in the GenBank sequence data base, Accession number M76559 (Williams, M. E. et al., *Neuron* 8:71–84 (1992)).

A. Isolation of Primary Clones and Generation of clone pNK-Hα2

The clone pNK-Hα2, was constructed as a fusion of two PCR clones. The template was human cerebellum Quick-Clone (Clonetech) cDNA, and the two PCR clones included sequences from 16–1409 (p2110) and from 1379–3313 (p2223). They were isolated as T/A clones in PCRII (Invitrogen) with the polylinker NotI site at the 5' end of each clone. p2110 was restricted with EcoRI and NsiI, and p2223 was restricted with NsiI and KpnI. The gel-purified inserts were fused at the NsiI site (Pos. 1394) and cloned into an EcoRI/KpnI restricted pNK-CMV vector. The SacI site is at the 5' end.

This clone, pNK-Hα2, contained certain alterations from a previously identified α2 sequence described in the GenBank sequence data base, Accession number M76559. These alterations are summarized in Table II.

TABLE II

Alterations in Hα2δ

| Position | Nucleotide Change | Amino Acid Change |
|---|---|---|
| 329 | A to C | Ser to Arg |
| 1191 | G to C | Arg to Thr |
| 1219 | G to C | Glu to Asp |
| 1596 | T to C | Gln to Arg |

TABLE II-continued

Alterations in Hα2δ

| Position | Nucleotide Change | Amino Acid Change |
|---|---|---|
| 1980 | T to C | Ile to Thr |
| 2090 | A to G | Asn to Asp |
| 3261 | A to G | Val to Ala |

B. Expression Clones

Two expression clones were generated. First, pNK-Hα2 was cut with KpnI and blunt ended. EcoRI linkers were attached. The reaction was treated with EcoRI, and the 3.3 kb EcoRI insert was isolated. This EcoRI insert was ligated into two different vectors, pED, and pBabe-CMV, which had been restricted with EcoRI. The correct orientations were selected. The resultant expression clones are referred to herein as pBabe-Hα2 and pED-Hα2.

EXAMPLE 3

Isolation and Expression of Clones for Human $\beta_3$ Subunit of N-Type Channel Sequences referred to herein are described in comparison to the sequence encoding an β3 subchannel, described in the GenBank sequence data base, Accession number L27584 (see Collin, T. et al., *Eur. J. Biochem.* 220(1):257–262 (1994)).

A. Isolation of Primary Clones and Generation of Clone pNK-Hβ3

A blunt ended PCR product spanning sequences 21–1490 was cloned into the EcoRI site of pSK-. The template was human cerebellum QuickClone (Clonetech) cDNA, generating pSK-Hβ3. The EcoRI/KpnI insert of pSK-Hβ3 was isolated and subsequently subcloned into the EcoRI/KpnI sites of pNK-CMV. The SacI site of the polylinker is at the 5' end.

This clone, pNK-Hβ3, contained certain alterations from a previously identified β3 sequence described in the HUM-CALBA Genbank file. These alterations are summarized in Table III.

TABLE III

Alterations in Hβ3

| Position | Nucleotide Change | Amino Acid Change |
|---|---|---|
| 46 | C to G | Leu to Val |
| 119 | TCC insertion | Ser insertion |
| 203 | A to T | Glu to Val |
| 300 | C to T | no change |
| 303 | C to G | no change |
| 420 | A to G | no change |
| 438 | C to T | no change |
| 477 | T to C | no change |
| 486 | T to G | no change |
| 534 | G to A | no change |
| 552 | A to C | no change |
| 561 | G to T | no change |
| 978 | ATG insertion | Met insertion |
| 1064 | T to A | Leu to His |
| 1283–4 | CG to GC | Thr to Ser |
| 1308 | C to T | no change |

EXAMPLE 4

Demonstration of Formation of Calcium Channels

CHODUX cells (Mitchell, P. J. et al., *Mol. Cell Bio.* 6(6):1926–35 (1986), Genbank M13476, M13477) were seeded on 100 mm dishes with 1 to 2×10$^6$ cells, at 24 hours before transfection. Cells were transformed with each of the following three expression clones: pNK-Hα1, pNK-Hα2, and pNK-Hβ3, using CaPO$_4$ transfection kit (Stratagene Mammalian Transfection Kit) according to the manufacturer's instructions. Cells were then washed using a single PBS wash, being careful not to dislodge cells. Thirty to 35 μg DNA was used per plate, in an approximately 2:1:1 subunit ratio (20 μg α1B, 7.5 μg α2δ, 5 μg β3). Transfection was allowed to proceed for approximately 16 hours overnight.

Saturating binding experiments were performed on the cells using a protocol as described by Harpold el al. (*Science* 257:389–395 (1992)). Briefly, reaction tubes containing $^{125}$I-omega-conotoxin GVIA (NEN) were prepared. The $^{125}$I-omega-conotoxin GVIA is packaged in vials of 10 μCi at a specific activity of 2200 Ci/mmol. The vial is resuspended in 450 μl water, to obtain 10 nM. For a 200 pM (saturating) final concentration, 10 μl/0.5 ml reaction was used. Cells were washed 1× with PBS and resuspended with 1–2 ml binding buffer and BSA per plate by pipetting. Approximately 500,000 cells (50–100 μ) per 0.5 ml reaction were used to initiate binding reaction. The reaction was allowed to proceed for 30–60 minutes at 37° C. Subsequently, 1 ml cold wash buffer+BSA was added, and cells were pelleted by 5 minutes at 2.8 krpm at 4° C. (Sorvall RT6000). Cells were washed 1× with 2 ml cold wash buffer+BSA and resuspended by gently vortexing; subsequently, they were repelleted. After aspiration of liquid, scintillation counting was performed. Results of the experiments demonstrated specific omega-conotoxin GVIA binding to whole cells. Specific binding indicates that the expression clones were expressed, and that the expressed subunits formed calcium channels.

EXAMPLE 5

Demonstration of Inhibition of omega-Conotoxin GVIA-Sensitive Potassium-Stimulated Calcium Uptake The uptake of $^{45}$Ca into cells was performed by an adaptation of the method of Tan, K. and A. H. Tashjian (*J. Biol. Chem.* 259:418–426 (1984). The principle of the method involves activating ion permeation through synaptosomal calcium channels by high potassium-induced depolarization of the synaptosomal preparation. The uptake of $^{45}$Ca measured by this procedure is mediated by N-type calcium channels, and is sensitive to dihydropyridine, phenylalkylamine, and benzothiazipine Ca antagonists at therapeutically relevant concentrations (Tan and Tashjian, ibid.)

Cells were transfected with the three human calcium channel subunits described herein. Transfected cells were suspended in 15 ml growth medium (Ham's F-10 medium plus 15% heat-inactivated horse serum and 2.5% heat-inactivated fetal bovine serum). The cells were centrifuged, resuspended, and then added to T-75 flasks containing 12–15 mls growth medium, and incubated at 37° C. for approximately one week. The cells were then removed from the flask after dissociation from the walls of the flask by treatment for 5 minutes at 37° C. with 10 μM EDTA in phosphate buffered saline. The buffer was decanted, and the cells were resuspended in approximately 200 ml of growth medium. The cells were then aliquoted 200 μg/well) into each well of several 96-well plates, and grown under the aforementioned conditions for 3–4 weeks, with replacement of growth medium occurring twice per week. Cells were fed growth medium 24 hours before they are employed for $^{45}$Ca uptake determinations.

At the time of the assay, media was aspirated from each 96-well plate using a manifold designed to allow 50 μL of liquid to remain in each well. Each plate was washed and aspirated twice with a low K+buffer solution "LKHBBS" (in mM: 5 KCl, 145 NaCl, 10 Hepes, 1 $MgCl_2$, 0.5 $CaCl_2$, 10 glucose, pH7.4), 200 μl/well. Each plate was incubated for 10 minutes at 37° C., and aspirated as above. To each well of each plate, 50 μl of LKHBBS containing the agent in twice the final concentration was added. The agents added are set forth in Table IV.

TABLE IV

Agents Added to Transfected Cells, Demonstrating omega-Conotoxin GVIA-Sensitive Potassium-Stimulated Calcium Uptake

| Sample | Cell Type | Agent Added |
|---|---|---|
| 1 | HEK293 | Control (no agent) |
| 2 | HEK293 | 75 mM KCl |
| 3 | T9 | Control (no agent) |
| 4 | T9 | 74 mM KCl |
| 5 | T9 | SNX-111 (10 μM) |
| 6 | T9 | SNX-111 (10 μM) plus KCl (negative control) |
| 7 | T9 | gadolinium (10 μM) |
| 8 | T9 | gadolinium (10 μM) plus KCl (negative control) |

The plates were incubated for 10 minutes at room temperature. To each well of each plate, 50 μl of either of two solutions were added: (a) LKHBBS containing 1 μCi of carrier-free $^{45}Ca$, or (b) HKHBBS (a high K+buffer containing 150 mM KCl and no NaCl, but otherwise identical to LKHBBS).

Each plate was then incubated for 5 minutes at room temperature, aspirated as above, and quenched with 200 μl/well of Quench Buffer (Ca-free LKHBBS containing 10 mM Tris-EGTA). Each plate was aspirated and rinsed with Quench Buffer a second time, then carefully aspirated to dryness. To each well of each plate 100 μl of High Safe II scintillation fluid (MicroScint (Packard)) was added. The plates were sealed, shaken, and subjected to scintillation spectrophotometry on a Microbeta 96-well Scintillation Counter (Wallae, Gaithersburg, Md., U.S.A.). Average counts per minute (CPM) are plotted in the FIGURE (numbering of data points corresponds to the numbering of agents in Table IV). Results indicated that omega-conotoxin GVIA-sensitive potassium-stimulated calcium uptake occurred in the transfected cells, and was inhibited by the agents known to inhibit L-type calcium channels, thereby demonstrating that the three subunits formed a functioning calcium channel.

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. An isolated calcium channel α1B subunit comprising SEQ ID NO: 2.

2. The isolated calcium channel subunit of claim 1, wherein nucleic acid encoding said calcium channel subunit is isolatable from human cerebellum tissue.

3. An antibody to the calcium channel subunit of claim 1.

4. A fusion protein comprising the calcium channel of claim 1.

5. An isolated calcium channel β3 subunit comprising SEQ ID NO: 6 having an alteration of $glu^{34} \rightarrow val^{34}$.

6. The isolated calcium channel of claim 5, wherein nucleic acid encoding said calcium channel subunit is isolatable from human cerebellum tissue.

7. An antibody to the calcium channel subunit of claim 5.

8. A fusion protein comprising the calcium channel subunit of claim 5.

9. An isolated calcium channel α2δ subunit comprising SEQ ID NO: 4 having at least one of the following alterations: $ser^{99} \rightarrow arg^{99}$; $arg^{386} \rightarrow thr^{386}$; $glu^{395} \rightarrow asp^{395}$; $ile^{649} \rightarrow thr^{649}$; $asn^{686} \rightarrow asp^{686}$ and $gln^{1076} \rightarrow arg^{1076}$.

10. The isolated calcium channel subunit of claim 9, wherein nucleic acid encoding said calcium channel subunit is isolatable from human cerebellum tissue.

11. An antibody to the calcium channel subunit of claim 9.

12. A fusion protein comprising the calcium channel subunit of claim 9.

13. An isolated human calcium channel comprising at least one subunit selected from the group consisting of:
   a) a first protein, comprising SEQ ID NO: 2
   b) a second protein, comprising SEQ ID NO: 4 having at least one of the following alterations: $ser^{99} \rightarrow arg^{99}$; $arg^{386} \rightarrow thr^{386}$; $glu^{395} \rightarrow asp^{395}$; $ile^{649} \rightarrow thr^{649}$; $asn^{686} \rightarrow asp^{686}$ and $gln^{1076} \rightarrow arg^{1076}$; and
   c) a third protein comprising SEQ ID NO: 6 having an alteration of $glu^{34} \rightarrow val^{34}$.

14. A method of identifying an agent which modulates the activity of a calcium channel, comprising the steps of:
   a) maintaining a host cell that expresses a functional calcium channel in a solution containing the agent to be tested and a calcium channel-selective ion, wherein the functional calcium channel comprises at least one of: an α1B subunit comprising SEQ ID NO: 2 a β3 subunit comprising SEQ ID NO: 6 having an alteration of $glu^{34} \rightarrow val^{34}$ and an α2δ subunit comprising SEQ ID NO: 4 having at least one of the following alternations: $ser^{99} \rightarrow arg^{99}$; $arg^{386} \rightarrow thr^{386}$; $glu^{395} \rightarrow asp^{395}$; $ile^{649} \rightarrow thr^{649}$; $asn^{686} \rightarrow asp^{686}$ and $gln^{1076} \rightarrow arg^{1076}$,
   b) depolarizing the cell membrane of the host cell; and
   c) detecting the current flowing into the cell, wherein if the current that is detected differs from that produced by a control cell maintained in a solution containing the calcium channel-selective ion, but not the agent to be tested, then the agent is an agent which modulated calcium channel activity.

* * * * *